United States Patent [19]
Teng et al.

[11] Patent Number: 5,948,613
[45] Date of Patent: Sep. 7, 1999

[54] METHODS OF SCREENING FOR RISK OF CANCER USING HUMAN LACTOFERRIN DNA PROBE OR PRIMER

[75] Inventors: Christina Teng, Raleigh, N.C.; Timothy J. Panella, Knoxville, Tenn.

[73] Assignee: The United States of America as represented by the Department of Health and Human Services, Washington, D.C.

[21] Appl. No.: 08/655,640

[22] Filed: May 30, 1996

Related U.S. Application Data

[62] Division of application No. 08/366,006, Dec. 28, 1994, abandoned, which is a continuation of application No. 07/992,538, Dec. 17, 1992, abandoned, which is a division of application No. 07/707,502, May 31, 1991, abandoned.

[51] Int. Cl.$^6$ .............................. C12Q 1/68; C12P 19/34
[52] U.S. Cl. ............................ 435/6; 435/91.2; 435/91.5
[58] Field of Search .............................. 435/6, 810, 91.2, 435/91.5

[56] References Cited

U.S. PATENT DOCUMENTS

| | | | |
|---|---|---|---|
| 4,683,195 | 7/1987 | Mullis | 435/6 |
| 5,026,651 | 6/1991 | Bowman | 435/320.1 |

FOREIGN PATENT DOCUMENTS

| | | |
|---|---|---|
| 9103642 | 11/1990 | WIPO . |
| 9108216 | 6/1991 | WIPO . |
| 9113982 | 9/1991 | WIPO . |

OTHER PUBLICATIONS

Anderson, B., et al. (1989) Structure of human lactoferrin: crystllographic structure analysis and refinement at 2.8 A resolution. J. Mol. Biol. 209:711–734.
Arnold, R., et al. (1977) A bactericidal effect for human lactoferrin. Science 197:263–265.
Bezwoda, W., et al. (1985) Enzyme linked immunosorbent assay for lactoferrin. Plasma and tissue measurements Clinica Chimica Acta 151:61–69.
Birgens, H. (1984) The biological significance of lactoferrin in haematology. Scand. J. Haematol., 33:225–230.
Broxmeyer, H., et al. (1987) The opposing actions in vivo on murine myelopoiesis of purified preparations of lactoferrin and the colony stimulating factors. Blood Cells 13:31–48.
Charpin, C., et al. (1985) Localization of lactoferrin and nonspecific cross–reacting antigen in human breast carcinomas. Cancer 55:2612–2617.
Das, M., et al. (1976) Human milk samples from different ethnic groups contain RNase that inhibits, and plasm membrane that stimulates, reverse transcription. Nature 262:802–805.
Ellison, R., et al. (1988) Damage of the outer membrane of enteric gram–negative bacteria by lactoferrin and transferrin. Infect Immun., 56:2774–2781.
Furmanski, P., et al. (1989) Multiple molecular forms of human lactoferrin. J. Exp. Med. 170:415–429.
Furmanski, P., et al. (1990) Multiple forms of lactoferrin in normal and leukemic human granulocytes. Exp. Hematol. 18:932–935.
Kijlstra, A., et al. (1989) Gel electrophoresis of human tears reveals various forms of tear lactoferrin. Current Eye Res., 8:581–588.
Liu, Y., and Teng, C.T., (1992) Estrogen response module of the mouse lactoferrin gene contains overlapping chicken ovalbumin upstream promoter transcription factor and . . . Mol. Endocrinol. 6(3):355–364.
Liu, Y., and Teng, C., (1991) Characterization of estrogen–responsive mouse lactoferrin promoter. J. Biol. Chem. 266(32):21880–21885.
Lomax, K., et al. (1989) Selective defect in myeloid cell lactoferrin gene expression in neutrophil specific granule deficiency. J. Clin. Invest. 83:514–519.
Lonnerdal, B., et al. (1976) The protein content of human milk. I. A transversal study of swedish normal material. Nutrition Report Int., 13:125–134.
Luckow, V., et al. (1988) Trends in the development of baculovirus expression vectors. BioTechnology 6:47–55.
Mason, D., and Taylor, C. (1978) Distribution of transferrin, ferritin, and lactoferrin in human tissues. J. Clin. Path. 31:316–327.
Masson, P., et al. (1969) Lactoferrin, an iron–binding protein NI neutrophilic leukocytes. J. Exp. Med., 130:643–658.
Metz–Boutigue, M.H., et al. (1981) The present state of the human lactotransferrin sequence. Study and Alignment of the cyanogen bromide fragments and characterization on N–and C–terminal domains. Biochimica et Biophysica Acta 670:243–254.
Panella, T., et al. (1991) Polymorphism and altered methylation of the lactoferrin gene in normal leukocytes, leukemic cells, and breast cancer. Cancer Research 51:3037–3043.
Pentecost, B., and Teng, C. (1987) Lactotransferrin is the major estrogen inducible protein of mouse uterine secretions, Biol. Chem. 262:10134–10139.
Powell, M., et al. (1990) Nucleotide sequence of human lactoferrin cDNA. Nucl. Acids Res. 18(13):4013.
Rado, T., et al. (1987) Isolation of lactoferrin cDNA from a human myeloid library and expression of mRNA during normal and leukemic myelopoiesis. Blood 70(4):989–993.
Rey, M., et al. (1990) Complete nucleotide sequence of human mammary gland lactoferrin. Nucl. Acids Res. 18(17):5288.

(List continued on next page.)

*Primary Examiner*—Carla J. Myers
*Attorney, Agent, or Firm*—Knobbe, Martens, Olson & Bear, LLP

[57] ABSTRACT

The present invention relates to a human lactoferrin cDNA obtained from human breast tissue and the protein encoded therefrom. The present invention further relates to methods for detecting malignancy arising from tissues that normally secrete lactoferrin using the cDNA gene probe of the present invention. Another aspect of the present invention relates to the promotor region that regulates the human lactoferrin gene.

9 Claims, 14 Drawing Sheets

OTHER PUBLICATIONS

Suggs, S., et al. (1981) Use of synthetic olignucleotides as hybridization probes: isolation of cloned cDNA sequences for human $B_2$–microglobulin. Proc. Natl. Acad. Sci. 78(11):6613–6617.

Summers, M., et al. (1987) A manual of methods for baculovirus vectors and insect cell culture procedures. Texas Agricultural Experiment Station Bulletin No. 1555.

Teng, C., et al. (1992) Differential molecular mechanism of the estrogen action that regulates lactoferrin gene inhuman and mouse. Molecular Endocrinology 92:1969–1981.

Teng, C., et al. (1989) Lactotransferrin gene expression in the mouse uterus and mammary gland. Endocrinology 124:992–999.

Young, R., et al. (1983) Efficient isolation of genes by using antibody probes. Proc. Natl. Acad. Sci. 80:1194–1198.

Lomax. 1989 J. Clinical Investigation 83:514–519.

Campbell 1992 British Journal of Cancer 65:19–26.

```
  1   CTT GTC TTC CTC GTC CTG CTG TTC CTC GGG GCC CTC GGA CTG TGT CTG GCT GGC CGT AGG
      Leu Val Phe Leu Val Leu Leu Phe Leu Gly Ala Leu Gly Leu Cys Leu Ala Gly Arg Arg

61   AGA AGG AGT GTT CAG TGG TGC TGC GTA TCC CAA GAG CCC ACA AAA TGC TTC CAA TGG
      Arg Arg Ser Val Gln Trp Cys Cys Val Ser Gln Glu Pro Thr Lys Cys Phe Gln Trp
                                          Ala                                  Asn

121   CAA AGG AAT ATG AGA AAA GTG CGT GGC CCT GTC AGC TGC ATA AAG AGA GAC TCC CCC
      Gln Arg Asn Met Arg Lys Val Arg Gly Pro Val Ser Cys Ile Lys Arg Asp Ser Pro
                                                                Leu

181   ATC CAG TGT ATC CAG GCC ATT GCG GAA AAC AGG GCC GAT GCT GTG ACC CTT GAT GGT GGT
      Ile Gln Cys Ile Gln Ala Ile Ala Glu Asn Arg Ala Asp Ala Val Thr Leu Asp Gly Gly

241   TTC ATA TAC GAG GCA GGC CTG GCC CTG TAC AAA TAT TAT GCC GTA GCG GCG GAA GTC TAC
      Phe Ile Tyr Glu Ala Gly Leu Ala Leu Tyr Lys Tyr Tyr Ala Val Ala Ala Glu Val Tyr

301   GGG ACC GAA AGA CAG CCA CGA ACT CAC TAT CAC GTG GCT GTG GTG AAG AAG GGC GGC
      Gly Thr Glu Arg Gln Pro Arg Thr His Tyr His Val Ala Val Val Lys Lys Gly Gly

361   AGC TTT CAG CTG AAC CTG CAA GGT CTG CTG AAG CTG TCC CAC ACA GGC CTT CGC AGG ACC
      Ser Phe Gln Leu Asn Leu Gln Gly Leu Leu Lys Leu Ser His Thr Gly Leu Arg Arg Thr
                                     C

421   GCT GGA TGG AAT GTC CCT ATA GGG ACA CTT CGT CCA TTC TTG AAT TGG ACG GGT CCA CCT
      Ala Gly Trp Asn Val Pro Ile Gly Thr Leu Arg Pro Phe Leu Asn Trp Thr Gly Pro Pro
                              Thr

481   GAG CCC ATT GAG GCA GCT GTG GCC AGG TTC TTC TCA GCC AGC TGT GTT CCC GGT GCA GAT
      Glu Pro Ile Glu Ala Ala Val Ala Arg Phe Phe Ser Ala Ser Cys Val Pro Gly Ala Asp
```

FIG. 10A

```
541  AAA GGA CAG TTC CCC AAC CTG TGT CGC CTG TGT GCG GGG ACA GGG GAA AAC AAA TGT GCC
     Lys Gly Gln Phe Pro Asn Leu Cys Arg Leu Cys Ala Gly Thr Gly Glu Asn Lys Cys Ala

601  TTC TCC CAG GAA CCG TAC TTC TTC AGC TAC TCT GGT GCC TTC AAG TGT CTG AGA GAC GGG
     Phe Ser Ser Gln Glu Pro Tyr Phe Phe Ser Tyr Ser Gly Ala Phe Lys Cys Leu Arg Asp
                                                                                 Lys

661  GCT GGA GAC GTG GCT TTT ATC AGA GAG AGC ACA GTG TTT GAG GAC CTG TCA GAC GAG GCT
     Ala Gly Asp Val Ala Phe Ile Arg Glu Ser Thr Val Phe Glu Asp Leu Ser Asp Glu Ala

721  GAA AGG GAC GAG TAT GAG TTA CTC CTG TGC CCA GAC AAC ACT CGG AAG CCA GTG GAC AAG TTC
     Glu Arg Asp Glu Tyr Glu Leu Leu Leu Cys Pro Asp Asn Thr Arg Lys Pro Val Asp Lys Phe

781  AAA GAC TGC CAT CTG CTG GCC CGG CGA GTT GCA CAT GCC AGT CGA GCT GTG AAT GGC
     Lys Asp Cys His Leu Leu Ala Arg Arg Val Ala His Ala Ser Arg Ser Val Asn Gly

841  AAG GAG GAT GCC ATC TGG AAT CTT CTC CGC CAG CAG CAG GAA AAG TTT GGA AAG GAC AAG
     Lys Glu Asp Ala Ile Trp Asn Leu Leu Arg Gln Gln Gln Glu Lys Phe Gly Lys Asp Lys

901  TCA CCG AAA TTC CAG CTC TTT GGC AGT CCT TCC CGC TCC CCT AGT GGG CAG AAA GAT CTG CTG TTC AAG GAC
     Ser Pro Lys Phe Gln Leu Phe Gly Ser Pro Ser Arg Ser Pro Ser Gly Gln Lys Asp Leu Leu Phe Lys Asp

961  TCT GCC ATT GGG TTT TCG AGG GTG CCC CCG AGG ATA TCT GGG CTG TAC CTT GGC TCC
     Ser Ala Ile Gly Phe Ser Arg Val Pro Pro Arg Ile Ser Gly Leu Tyr Leu Gly Ser

1021 GGC TAC TTC ACT GCC ATC CAG AAC TTG AGG AAA AGT GAG GAG GTG GCT GCC CGG CGT
     Gly Tyr Phe Thr Ala Ile Gln Asn Leu Arg Lys Ser Glu Glu Val Ala Ala Arg Arg
```

*FIG. 10B*

```
1081  GCG CGG GTC GTG TGG TGT GCG GTG GGC GAG CTG CGC AAG TGT AAC CAG TGG AGT
      Ala Arg Val Val Trp Cys Ala Val Gly Glu Leu Arg Lys Cys Asn Gln Trp Ser

1141  GGC TTG AGC GAA GGC AGC GTG ACC GTG TCC TCG GCC ACC AAG TGT GAC ATC GCC
      Gly Leu Ser Glu Gly Ser Val Thr Val Ser Ser Ala Thr Lys Cys Asp Ile Ala

1201  CTG GTG CTG AAA GGA GAA GCT GAT GCC ATG AGT TTG GAT GGA TAT GTG TAC ACT GCA
      Leu Val Leu Lys Gly Glu Ala Asp Ala Met Ser Leu Asp Gly Tyr Val Tyr Thr Ala
         T

1261  GGC AAA TGT GGT TTG GTG CCT GTC CTG GCA GAG AAC TAC AAA TCC CAA CAA AGC AGT GAC
      Gly Lys Cys Gly Leu Val Pro Val Leu Ala Glu Asn Tyr Lys Ser Gln Gln Ser Ser Asp
      Cys

1321  CCT GAT CCT AAC TGT GTG GAT AGA CCT GTG GAA GGA GGG TAT CTT GCT CTT GCT GTG AGG
      Pro Asp Pro Asn Cys Val Asp Arg Pro Val Glu Gly Tyr Leu Ala Val Val Arg

1381  AGA TCA GAC ACT AGC AGC CTT ACC TGG TGG AAC TCT GTG AAG GGC AAG AAG TCC CAC TGC ACC GCC
      Arg Ser Asp Thr Ser Ser Leu Thr Trp Trp Asn Ser Val Lys Gly Lys Lys Ser His Cys Thr Ala

1441  GTG GAC AGG ACT GCA GGC TGG AAT ATC CCC ATG GGC CTG CTC TTC AAC CAG ACG GGC TCC
      Val Asp Arg Thr Ala Gly Trp Asn Ile Pro Met Gly Leu Leu Phe Asn Gln Thr Gly Ser
                      CG
                      Ala

1501  TGC AAA TTT GAT GAA TAT TTC AGT CAA AGC TGT GCC CCT GGG TCT GAC CCG AGA TCT AAT
      Cys Lys Phe Asp Glu Tyr Phe Ser Gln Ser Cys Ala Pro Gly Ser Asp Pro Arg Ser Asn

1561  CTC TGT GCT CTG TGT ATT GGC GAC GAG CAG GGT GAG AAT AAG TGC GTG CCC AAC AGC AAC
      Leu Cys Ala Leu Cys Ile Gly Asp Glu Gln Gly Glu Asn Lys Cys Val Pro Asn Ser Asn
                                                                           T
```

FIG. 10C

```
1621 GAG AGA TAC TAC ACT GGC TAC ACT GGG GCT TTC CGG TGC CTG GCT GAG AAT GCT GGA GAC GTT
     Glu Arg Tyr Tyr Thr Gly Tyr Thr Gly Ala Phe Arg Cys Leu Ala Glu Asn Ala Gly Asp Val

1681 GCA TTT GTG AAA GAT GTC ACT GTC TTG CAG AAC ACT GAT GGA AAT AAC AAT GAG GCA TGG
     Ala Phe Val Lys Asp Val Thr Val Leu Gln Asn Thr Asp Gly Asn Asn Asn Glu Ala Trp

1741 GCT AAG GAT TTG AAG CTG GCA GAC TTT GCG CTG TGC CTC GAT GGC AAA CGG AAG CCT
     Ala Lys Asp Leu Lys Leu Ala Asp Phe Ala Leu Cys Leu Asp Gly Lys Arg Lys Pro

1801 GTG ACT GAG GCT AGA AGC TGC CAT CTT GCC AAT CCG GCC ATG CAT GCC GTG GTG TCT CGG
     Val Thr Glu Ala Arg Ser Cys His Leu Ala Asn Pro Ala Met His Ala Val Val Ser Arg
                                                     C

1861 ATG GAT AAG GTG GAA CGC CTG AAA CAG GTG TTG CTC CAC CAA CAG GCT AAA TTT GGG AGA
     Met Asp Lys Val Glu Arg Leu Lys Gln Val Leu Leu His Gln Gln Ala Lys Phe Gly Arg

1921 AAT GGA TCT GAC TGC CCG GAC AAG TTT TGC TTA TTC CAG TCT GAA ACC AAA AAC CTT CTG
     Asn Gly Ser Asp Cys Pro Asp Lys Phe Cys Leu Phe Gln Ser Glu Thr Lys Asn Leu Leu

1981 TTC AAT GAC AAC ACT GAG TGT CTG GCC AGA CTC CAT GCC AGA CTC CAT GGC AAA ACA ACA TAT GAA AAA TAT
     Phe Asn Asp Asn Thr Glu Cys Leu Ala Arg Leu His Gly Lys Thr Thr Glu Lys Tyr

2041 TTG GGA CCA CAG TAT GTC GCA GGC ATT ACT AAT CTG AAA AAG TGC TCA ACC TCC TCC
     Leu Gly Pro Gln Tyr Val Ala Gly Ile Thr Asn Leu Lys Lys Cys Ser Thr Ser Pro Ser
                                                                                C
                                                                               Leu

2101 TGG AAG CCT GTG AAT TC  2117
     Trp Lys Pro Val Asn
     Leu Glu Ala Cys Glu Phe
```

FIG. 10D

METHODS OF SCREENING FOR RISK OF CANCER USING HUMAN LACTOFERRIN DNA PROBE OR PRIMER

This application is a divisional of U.S. patent application Ser. No. 08/366,006, filed on Dec. 28, 1994, now abandoned which is a continuation of U.S. patent application Ser. No. 07/992,538, filed Dec. 17, 1992, abandoned, which is a divisional of U.S. patent application Ser. No. 07/707,502, filed May 31, 1991, abandoned.

BACKGROUND OF THE INVENTION

1. Field of the Invention

The present invention relates to a human lactoferrin gene isolated from breast tissue and to the protein product encoded therein. The present invention further relates to the promotor region of human lactoferrin gene and to methods for detecting and analyzing malignancies arising from tissues that normally secrete lactoferrin using a novel human lactoferrin cDNA gene sequence.

2. Background Information

Lactoferrin is a single polypeptide molecule (M, 76,000) with sites where two oligosaccharide chains can attach (B. F. Anderson et al., *J. Mol. Biol.* 209:711–734 (1989)). This protein shares significant homology with transferrin, however, its role in iron transport is limited since it binds iron 260 times stronger than transferrin (B. F. Anderson et al., (1989)). Two and possibly three isoforms of lactoferrin have been isolated using an affinity chromatography (P. Furnamski et al., *J. Exp. Med.* 170:415–429 (1989); A. Kijlstra et al., *Current Eye Res.*, 8:581–588 (1989)). Lactoferrin has been shown to inhibit bacterial growth by chelating iron and directly attacking the cell wall (R. T. Ellison et al., *Infect Immun.*, 56:2774–2781 (1988)), contribute to the anemia of chronic disease (Birgens. *Scand. J. Haematol.*, 33:225–230 (1984)), improve intestinal absorption of iron in infants (Birgens., (1984)) inhibit myelopoiesis (H. E. Broxmeyer et al., *Blood Cells* 13:31–48 (1987)), and degrade mRNA (P. Furmanski et al., (1989); M. R. Das et al., *Nature* 262:802–805 (1976); P. Furmanski and Z. P. Li, *Exp. Hematol* 18:932–935 (1990). Large quantities of lactoferrin are found in breast milk (B. Lonnerdal et al., *Nutrition Report Int.*, 13:125–134 (1976)), in estrogen-stimulated uterine epithelium (B. T. Pentecost and C. T. Teng, *J. Biol. Chem.* 262:10134–10139 (1987)), and in neutrophilic granulocytes (P. L. Masson et al., *J. Exp. Med.*, 130:643–658 (1969)) with smaller amounts in tears, saliva, serum, and seminal fluid (D. Y. Mason and C. R. Taylor, *J. Clin. Path.*, 31:316–327 (1978)).

While normal breast ductal epithelium and neutrophilic granulocytes contain lactoferrin, their malignant counterparts frequently do not (C. Charpin et al., *Cancer*, 55:2612–2617 (1985); T. A. Rado et al., *Blood*, 70:989–993 (1987)). This has been evaluated at the protein level and in a few samples at the messenger RNA level (T. A. Rado et al., (1987)). Analysis at the genomic level has not been performed. DNA variations, that are detected in the coding regions, may lead to abnormal protein structure and loss of normal function. Variations, such as mutations, deletions, or changes in methylation, at the promoter regions could lead to altered regulation of the gene. Evaluation of the lactoferrin gene may provide interesting insight concerning the production of lactoferrin in malignant cells. Thus, the need exists for the structure of the lactoferrin gene including the cDNA and the promotor region. The present invention provides such a description of the structure of a human lactoferrin cDNA and promotor region of the gene.

Using a lactoferrin cDNA clone isolated from human breast tissue, the applicants have evaluated restriction fragment length changes in DNA from the white blood cells of 10 normal controls, acute non-lymphocyte leukemia (ANLL) cells from 7 patients, T-cell acute lymphocyte leukemia (ALL) from one patient, 3 leukemia cell lines, and 7 breast cancer cell lines. A comparative study of the lactoferrin gene in these different cell types is provided herein.

The present invention further relates, in part, to a human lactoferrin cDNA and the protein product encoded therein. In another aspect, the present invention relates to methods for detecting malignancy in tissues that normally secrete lactoferrin by evaluating restriction patterns in DNA using a lactoferrin gene probe of the present invention.

SUMMARY OF THE INVENTION

It is an object of the present invention to provide a DNA sequence of the human lactoferrin gene including the cDNA and the promotor region and to the protein product encoded therein.

In one embodiment, the present invention relates to a DNA segment encoding human lactoferrin according to the sequence identification number 1. In another embodiment, the present invention relates to the human lactoferrin protein encoded by the sequences given in identification number 2.

In yet another embodiment, the present invention relates to a DNA segment of the promotor region for human lactoferrin according to the sequence identification number 5 and allelic variations thereof.

In a further embodiment, the present invention relates to a recombinant DNA construct comprising the DNA segments encoding the human lactoferrin gene sequences described above and a vector.

In another embodiment, the present invention relates to a recombinant DNA construct comprising the DNA segment encoding the human lactoferrin gene described above and a DNA promotor regulatory region for human lactoferrin according to sequence identification number 5 or portion thereof operatively linked to the DNA fragment.

In a further embodiment, the present invention relates to a host cell comprising the above described constructs.

Another embodiment of the present invention relates to a method of treating a condition in a patient characterized by a deficiency in lactoferrin by administering to the patient an amount of human lactoferrin according to the present invention in sufficient quantities to eliminate the deficiency. The conditions include neutropenia, AIDS, skin infection, gastrointestinal bacterial overgrowth syndrome, vaginal infection and septic shock.

In yet another embodiment, the present invention relates to methods of diagnosing malignancy or detecting the recovery of a malignancy from a biological sample comprising the steps of isolating DNA from the biological sample and from normal control samples, cutting the DNA with a restriction enzyme called Xba I, hybridizing the cut DNA with a DNA segment of the human lactoferrin gene of the present invention described above or portion thereof under conditions such that hybridization is effected and comparing the hybridization product patterns of the biological sample and the normal control sample with each other.

In a further embodiment, the present invention relates to a method for detecting small insertions, deletions or mutations surrounding the human lactoferrin gene comprising the steps of isolating the DNA from a biological sample suspected of having such an insertion, deletion or mutation, amplifying the DNA using the human lactoferrin gene segment of the present invention described above or portion thereof in a polymerase chain reaction followed by enzymatically cutting the amplified DNA with Xba I, and hybridizing this DNA with the human lactoferrin gene segment described above under conditions such that hybridization is effected and sequencing the hybridized DNA.

Various other objects and advantages of the present invention will become obvious from the drawings and detailed description of the invention.

The entire contents of all publications mentioned herein are hereby incorporated by reference.

BRIEF DESCRIPTION OF THE DRAWINGS

FIGS. 10A–10D depicts a sequence data of HLF 1212 (SEQ ID NO: 1). Differences between the published protein derived AA sequence and our cDNA derived sequence are indicated by underlining the extra AA in our sequence or indicating substitutions beneath our sequence. Nucleotide differences based on published sequence data are indicated above our sequence. Nucleotide changes resulting in a different AA are typed below the area of substitution.

DETAILED DESCRIPTION OF THE INVENTION

Figure 1A:
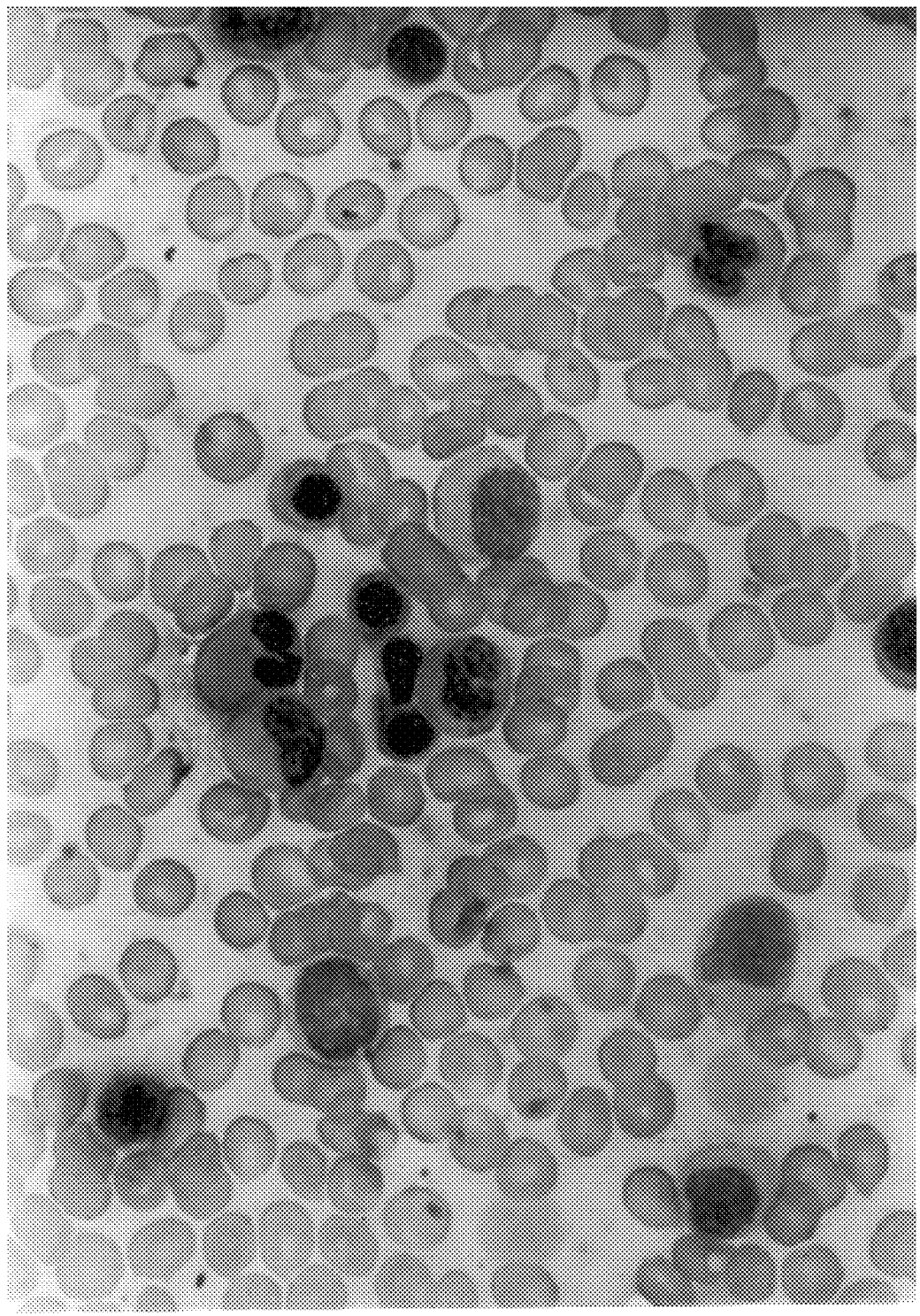
FIGS. 1A and 1B show the immunocytochemical staining of normal bone marrow (A)×400, and breast cancer cell line SKB R3 (B)×680 using anti-lactoferrin antibody at 1:1500.

The present invention relates to a cDNA sequence for human lactoferrin and the protein encoded therein. The cDNA called HLF1212 was isolated from human breast tissue and is 2117 kb in length. The sequence agrees with the modified amino acid sequence of iron-binding lactoferrin in all areas except the 3 sites in the N-terminal region. One further change is in arginine in place of a lysine at amino acid 200.

Another aspect of the present invention relates to methods for diagnosing malignancy by restriction fragment length polymorphisim (RFLP) analysis of DNA extracted from normal peripheral blood and leukemia cells from patients using the cDNA of the present invention as the probe. Southern analysis indicates that the human lactoferrin gene is polymorphic when tested using Msp I and Xba I restriction enzymes. Further analysis indicates that the changes in the XbaI recognition site could be explained by alterations in DNA caused by or resulting in malignancy. In the present invention, the DNA from normal and malignant cells are digested with XbaI and the fragment pattern compared using methods well known in the art. The Xba I restriction is associated with 4 patterns in normal and malignant cells (Example 3 and FIGS. 6 and 7). The most striking change is the deletion of many bands found only in DNA obtained from malignant cells or cell lines derived from either leukemia or breast cancer.

If the patterns found in Example 3 (Xba I RFLP pattern C+D) are found in women before breast cancer occurs, it may be easy to screen women at high risk of breast cancer for these changes using cDNA probe of the present invention and RFLP methodologies well known in the art. For example, lymphocytes may be separated from peripheral blood, DNA extracted, and cut with XbaI. This DNA can then be probed with HLF 1212 or a small piece of HLF 1212 and patterns determined. High risk patients may be placed on preventive medicines such as Tamoxifen retinoids or have surgery. The same may hold for other hormonally responsive tumors such as prostrate, uterus, or tumors arising from lactoferrin secreting organs such as leukemia, or salivary gland.

Another aspect of the present invention relates to RFLP methods to measure the prognosis of certain types of cancer patients that are given therapeutics. One may place patients with breast, prostate, uterine, or salivary cancer into risk groups. Those with a specific pattern may be at different risks of disease reoccurence. Thus, RFLP analysis using the cDNA probe of the present invention may provide prognostic information for patients with cancer.

Another aspect of the present invention relates to methods for detecting small insertions, deletions or mutations surrounding the human lactoferrin gene. Either of the above described RFLP methods could be combine with polymerase chain reaction (PCR) analysis. The abnormal area of the gene may be amplified using methods well known in the art and then mutations detected using restriction analysis (i.e. Xba I) and sequencing.

Yet another aspect of the present invention relates to methods for detecting tumors in pathological specimens that may contain too few malignant cells to be detected by standard methods. This method may involve PCR of DNA extracted from specimens (biopsy of tissue or bone marrow) and subsequent analysis using the RFLP techniques and DNA probes described above and in the Examples.

In another embodiment, the present invention relates to the cDNA clone for human lactoferrin called HLF 1213 and the protein encoded therein. The sequence of HLF 1213 (sequence ID NO:3) is a combination of clones HLF 1212 (sequence ID NO: 1), 031A (sequence ID NO: 5) and other clones isolated in the same method as HLF 1212. (See Example 2). This clone is a composite of the complete human lactoferrin cDNA. This clone may be constructed by splicing 2 clones together with HLF 1212 (031A, and HLF 1212). Both HLF 1212 or this combined fragment called HLF 1213 may be used to make recombinant human lactoferrin.

In another embodiment, the present invention relates to the human lactoferrin protein obtained from HLF 1212 and HLF 1213 called sequence ID Numbers 2 and 4 respectively.

In yet another embodiment, the present invention relates to recombinant human lactoferrin expressed in vitro through molecular genetic engineering technology.

The present invention also relates to the recombinant DNA molecules and to host cells transformed therewith. Using standard methodology well known in the art and described briefly below, a recombinant DNA molecule comprising a vector, for example, a Bacculovirus transfer vector and a DNA fragment encoding human lactoferrin, for example, HLF 1212 or 1213, can be constructed without undue experimentation.

The methods of choice is the Baculovirus-insect cell expression system (M. D. Summers and G. E. Smith, *Texas Agriculture Experiment Station Bulletin* No. 1555, (1987); V. A. Luckow et al., *Bio/technology* 6:47–55 (1988)). This system has been used successfully to produce commercial quantities of recombinant mammalian glycoproteins. Other expression systems known in the art can also be used to produce the recombinant protein, for example, yeast, bacterial or mammalian cells.

The 2.2 Kb Eco-R1 fragment containing the entire human lactoferrin coding region may be removed from plasmid HLF 1212 or HLF 1213. The lactoferrin cDNA may be subcloned into Baculovirus transfer vector pAc 700 series (T. Maniatis et al., *Molecular Cloning*: a laboratory manual, Cold Spring Harbor Laboratories, Cold Spring Harbor, N.Y.). Recombinant plasmid (Achlf) may be co-transfected into Sf9 cells along with wild-type AcNPV viral DNA by calcium phosphate transfection procedure (M. D. Summus and G. E. Smith). In vivo homologous recombination between the polyhedron sequences in the wild type viral DNA and the recombinant plasmid results in the generation of recombinatn viruses coding for a fused gene product. The recombinant viruses may be plaque purified by screening for the occlusion negative (polyhderon negative) phenotype or by colony hybridization using $^{32}$P-DNA probes covering the HLF-coding region. Characterization of the recombinant viral DNA may be carried out as described by Maniatis et al. Sf9 cells may be plated in 24-well dishes (Costar) at $3 \times 10^5$ cells/well and allowed to attach for 2 hours in complete Graces medium. Cells are then infected with wild type AcNPV or recombinant virus AchLF. Two days post-infection, the cell layer and the condition medium may be collected and assayed for the presence of hLF. HLF can be analyzed by SDA-PAGE and Western blotting. Iron binding capacity and anti-bacterial acitivity may also be examined.

The present invention further relates to treatment of antibacterial and antiviral infections using pharmaceutical doses of human lactoferrin of the present invention (HLF 1212 and 1213 corresponding to sequence ID Nos. 2 and 4 respectively) or recombinant human lactoferrin protein of the present invention.

The actions of lactoferrin are varied; the best established function is antibacterial (R. R. Arnold et al., *Science* 197:263–265 (1977)). Patients have been found whose neutrophils are deficient in lactoferrin (K. J. Lomax et al., *J. Clin. Invest.* 83:514–519 (1989)). These patients are prone to recurrent infections. Lactoferrin also has been found to decrease release of CSF or monokines, enhancement monocyte natural killer activity, enhancement of hydroxyl radical production and modulate the activation of the complement system (Birgens, *Scand. J. Haematol* 33:225–230 (1984)). There is also early in vivo evidence of lactoferrin antiviral activity.

In the past few years, HIV infection has become a significant health problem. HIV causes morbidity by crippling the body's defense mechanism and allowing development of opportunistic infections. Present treatment is less than ideal and involves treating opportunistic infections as they occur or inhibiting reverse transcriptase. Human lactoferrin is the natural product of the human defense machinery and has been given to patients both orally and intravenously with no side effects. Due to its bacteriocidal, antifungal, and immunoregulatory activity, administering pharmaceutical acceptable doses of lactoferrin of the present invention could prove an effective agent to treat patients with AIDS or patients with neutropenia.

Other possible uses of the human lactoferrin of the present invention include treatment of lactoferrin in pharmaceutical doses, either orally or intravenously to patients with skin infections (burn patients), gastrointestinal bacterial overgrowth syndromes, vaginal infections, septic shock, and numerous other disorders.

In yet another embodiment, the present invention relates to the genomic human lactoferrin promotor region (sequence ID No: 5). This sequence contains the entire human lactoferrin promotor region fragment including exon 1 of human lactoferrin clone 1212.

The 5' genomic regulatory region of the present invention has the ability to regulate DNA in a tissue specific manner, i.e., it can be on in breast tissue and off in skin. It also can be hormonally regulated, i.e., on in mid-cycle menstrual cycle, off at menses. This regulation ability may be used in several ways. Genes targeted for transgenic mice may use the lactoferrin promotor. Genes to be used in therapy of human disease (gene therapy) may be linked to the lactoferrin promotor and thus the therapeutic gene regulated in a tissue specific or hormonal pattern.

The invention is described in further detail in the following non-limited examples.

EXAMPLES

The following procedures and materials were used througout the Examples.

Human Tissue.

150 ml of heparinized blood or 5 ml heparinized bone marrow was obtained from normal paid donors after informed consent was obtained. Informed consent and leukemia cells were obtained from seven patients with acute leukemia undergoing emergent leukapheresis. The FAB classification of the patients were: two patients with M2, two patients with M7, and one patient each with M4, M7, ANLL not further specified, and T-cell ALL. Nucleated cells were obtained from 80 ml of blood from normal donors after first incubating cells at 37° C. for 30 min. in 1:20 diluted methylcellulose (30 g/500 ml Hank balanced salt solution (HBSS) to sediment the red blood cells. The leukocyte-rich fraction was removed, and centrifuged into a pellet at 500×g for 10 min. at 4° C. Cells from patients with leukemia were either used fresh or diluted in RPMI 1640 containing 20% fetal calf serum and 10% dimethylsulfoxide (DMSO), then frozen at −70° C. until use. Human leukocyte antigen (HLA) typing, cytogenetic analysis, and bone marrow biopsy results were available for all but one patient who died shortly after leukapheresis. All cell lines were originally obtained from ATCC® (Rockville, Md.) and maintained at 37° C., 93% humidity, and 5% $CO_2$. Breast cancer cell lines and HBL 100 (a cell line derived from a lactating breast) were maintained and provided by Dr. J. Dirk Iglehart (Department of Surgery, Duke University). Cells were grown to confluence and separated from dishes with trypsin 0.05%/EDTA (Gibco), washed, and centrifuged. For all samples, DNA was isolated according to standard methodology (W. M. Strauss in Current Protocols in Molecular Biology. F. A. Ausebel, et al., (eds.), pp. 2.2.1–2.2.3 1990. Greene Publishing and Wiley-Interscience, New York.

Isolation of cDNA

A Clonetech cDNA library from normal human breast tissue (HL 1037b) was plated in host cells Y1090, filter-lifted and probed with mouse lactoferrin cDNA T267 (B. T. Pentecost and C. T. Teng, (1987)). Positive clones were plaque-purified, and the inserts subcloned into the Eco R1 site of Bluescript II SK+ (Stratagene). The recombinant clones were transformed into XL1 Blue cells (Stratagene). A 2.1 Kb insert (HLF 1212) was isolated and sequenced using the dideoxy nucleotide termination reaction and $[^{35}S]dATP$ label under contract by Lark sequencing company.

Southern Analysis

Ten μg of DNA was digested at 37° C. for three hours with Eco R1, Bam H1, Hind III, Pvu II, Pst I, Msp I, Xba I, Hpa II, Mbo I or Sau 3AI under conditions specified by the manufacturer (BRL). Hpa II and Sau 3AI will not cleave DNA when specific bases within their recognition sites are methylated. Msp I and Mbo I respectively, recognize these same sites and are methylation insensitive. DNA was loaded into 0.7, 0.8, or 1.2% agarose gels, run overnight, and transferred either to Genescreen Plus (nylon, DuPont) or BA-S NC (nitrocellulose, Schleicher & Schuel). Lactoferrin cDNA was removed from plasmid with Eco R1, redigested with Pst I, and gel purified. Both fragments were labeled with $[^{32}P]PdCTP$ using a random primer kit (Stratagene) to a specific activity of $1×10^9$. Hybridization was performed exactly according to Genescreen instructions or a modification of BA-S NC instructions (hybridization solution—50% formamide, 5× SSPE, 1% SDS, 4× Denhardt, 100 μg/ml single stranded DNA, 7.5% dextran, pre-hybridization solution—the same as above with 5% formamide and no dextran). Filters were washed at high stringency at 60° C. and exposed to Kodak XOMAT AR film using intensifying screens for 3–7 days. DNA from normal and leukemic cells was probed with histone cDNA (Oncore) as a control; no polymorphic pattern was found.

Immunocytochemistry

Antibody against human milk lactoferrin (Sigma) was raised in rabbits and the IgG fraction was prepared as described previously (C. T. Teng et al., *Endocrinology* 124:992–999 (1989)). All cell lines, normal cells, and leukemia patient's cells were examined using this antibody. Ten normal bone marrow specimens were stained to define the specific cell in bone marrow that begins to produce lactoferrin. Cells were smeared onto alcohol-washed, pre-cleaned slides, air dried 1 hour, and fixed in 95% methanol, and 1.7% formalin for 10 min. Slides were next rinsed in $dH_2O$ and either air dried and stored in a moisture proof container at 4° C. or used immediately. Staining procedure was followed directions provided with Vector ABC-AP kit using levamisol as the blocking agent, antibody dilution of 1:1500, and hematoxylin (gill #3) counterstain. Three-hundred cells per sample were scored manually as negative, trace, or positive.

Example 1

Immunocytochemical Staining.

Figure 1B:
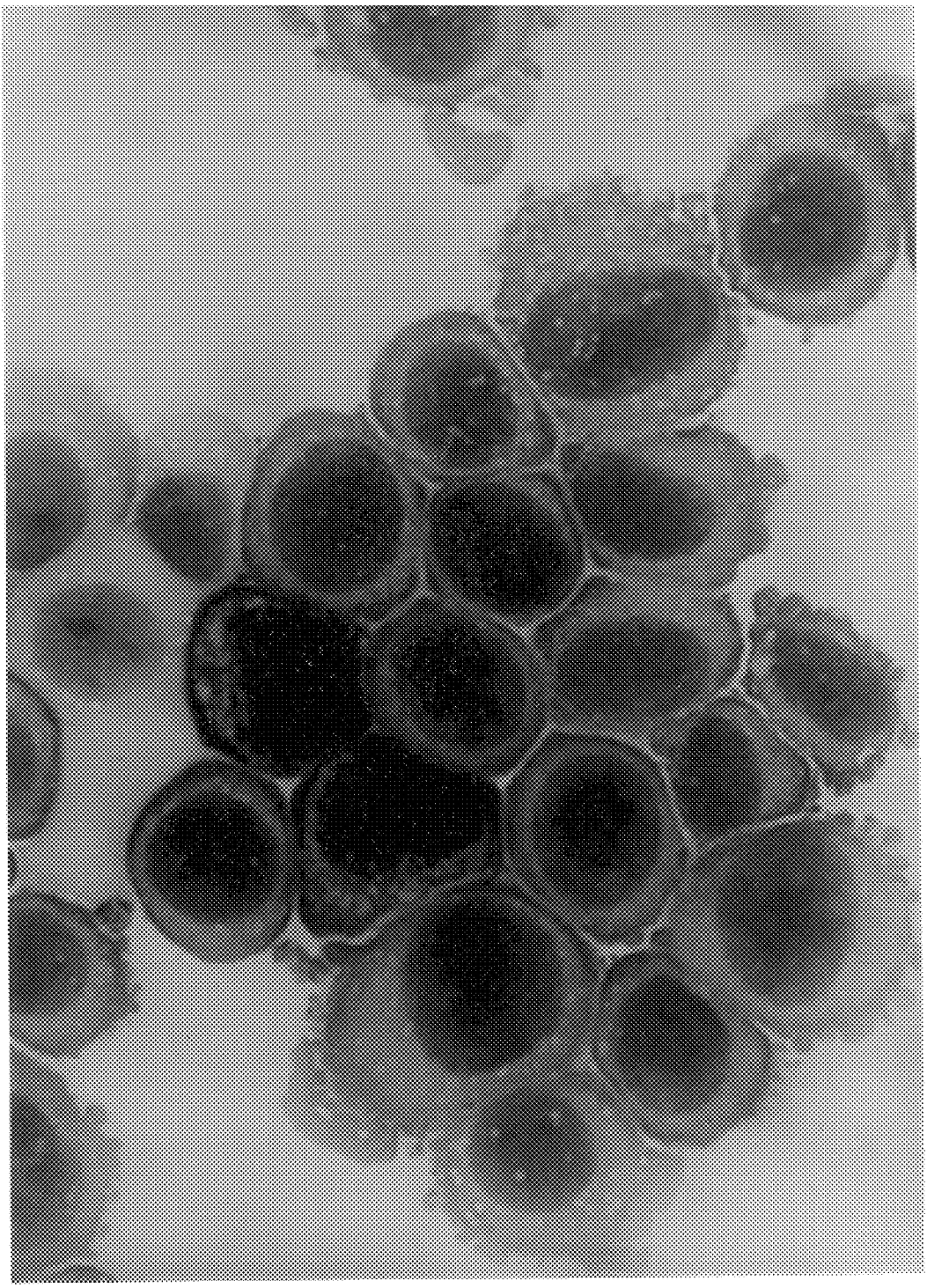

As shown in Table 1 and FIG. 1A, bone marrow lactoferrin began to appear in the myelocyte stage with almost all cells staining positively by the metamyelocyte stage. None of the leukemia cells from patients or leukemia cell lines contained stainable lactoferrin. Occasional positive granulocytes could be seen in with the leukemic cells from patients. Breast cancer cell lines stained negatively for lactoferrin except for 1.5% trace positive cells in SKB R3 (FIG. 1B).

TABLE 1

Immunocytochemical staining of normal bone marrow using anti-lactoferrin antibody

|  | Blasts and Promyelocytes | Myelocytes | Metamyelocytes | Bands | Neutrophils |
| --- | --- | --- | --- | --- | --- |
| Negative | 93%[a] (8.6) | 30% (20.4) | 12% (7.5) | 3% (1.2) | 1% (1) |
| Trace | 6% (8.2) | 38% (8.3) | 40% (10.6) | 10% (5.2) | 2% (2) |
| Positive | 0.3% (0.4) | 32% (19.2) | 48% (17) | 88% (4.5) | 97% (2) |

[a]values represent the mean of 10 bone marrow samples stained with the standard deviation in parenthesis, >300 cells counted per sample.

Example 2

Library Screening, Isolation and Characterization of HLF 1212 Clone.

Thirty human lactoferrin clones were isolated from the breast tissue cDNA library. The longest (HLF 1212) was sequenced completely. This clone is 2117 bp's in length and includes a 17 amino acid (AA) leader sequence (no ATG site) and is 4 AA shy of the 3' terminus (FIG. 10). The AA sequence coded for by HLF 1212 has 4 sites that differ from the previously published revised AA sequence derived from the protein (B. F. Anderson et al., (1989)). In the sequence of the present invention, there is one insertion (Arginine (Arg) at AA 22, bp 64-6) and three substitutions (Glutamine (Gln) for Asparagine (Asn) at AA 31, bp 91-3; Isoleucine (Ile) for Leucine (Leu) at AA 55, bp 163-5; and Arg for Lysine (Lys) at AA 218, bp 652-4). The first three of these changes are clustered at the 5' end. Contained within HLF 1212, but not in any of the 10 other partially sequenced isolates, is a deleted cytosine at bp 2097 (AA 699) which caused a frame-shift at the 3' end of the protein. This extra base was confirmed by repeated bi-directional sequencing. The deletion at 2097 is now thought to be either a cloning artifact or a rare species of mRNA.

In addition to cDNA of the present invention, three other authors have published lactoferrin cDNA sequence data (T. A. Rado, et al., (1987); M. J. Powell and J. E. Ogden, *Nucleic Acids Res.*, 18:4013, (1990); M. W. Rey et al., *Nucelic Acids Res.*, 18:5288, (1990)). All of these sequences are different, and a comparison between the AA data derived from the protein and sequence changes derived from the cDNA, are presented in FIG. 10. When compared to HLF 1212, all of the sequences contain an extra cytosine at bp 2097 (AA 699). Powell et al., (1990) isolated a 2.3 kb sequence from breast tissue that, except for the extra cytosine, is identical to our cDNA in the areas of overlap. The isolate of the present invention differs from that of Rado's 3' 1023 base fragment in 4 locations (T. A. Rado et al., (1987)) with one resulting difference in the AA sequence (Gly for Ala at AA 486, bp 1456-8). Two silent mutations and the extra cytosine make up the remainder of the changes. Ray et al have also published a cDNA sequence isolated from human mammary tissue that contains two AA changes (Ile for Thr at AA 147, bp 440–2; and Gly for Cys at AA 421, bp 1261–3) and one silent base difference (M. W. Rey et al., (1990)).

Example 3
Evaluation of Restriction Fragments using Lactoferrin HLF 1212 as Probe.

Figure 2:
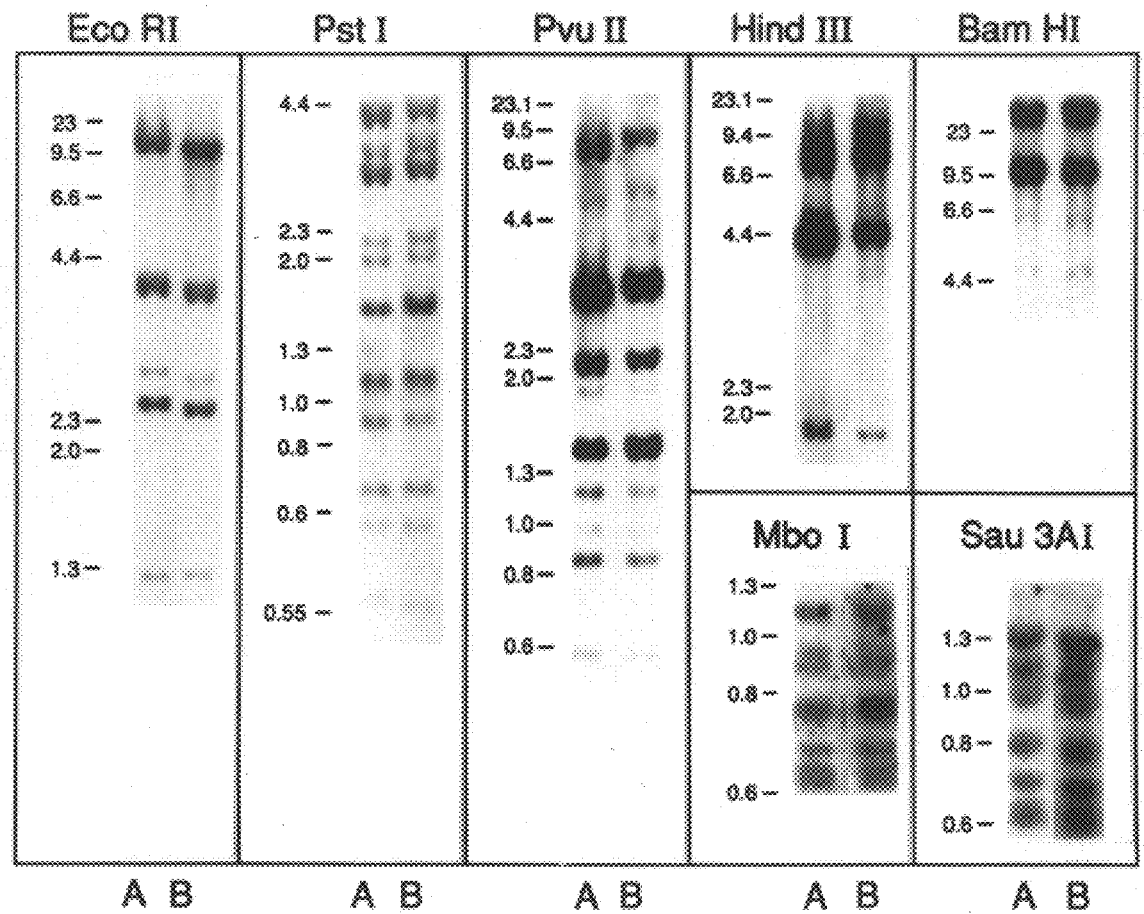
FIG. 2 depicts the restriction fragments produced with DNA from normal cells (A) or from leukemia cells (B) using lactoferrin cDNA (HLF 1212) as the probe. Normal samples (n=9) and DNA from 10 different leukemia cells types were digested with indicated enzyme, run in one gel and representative lanes cut out for comparison.
Figure 3:
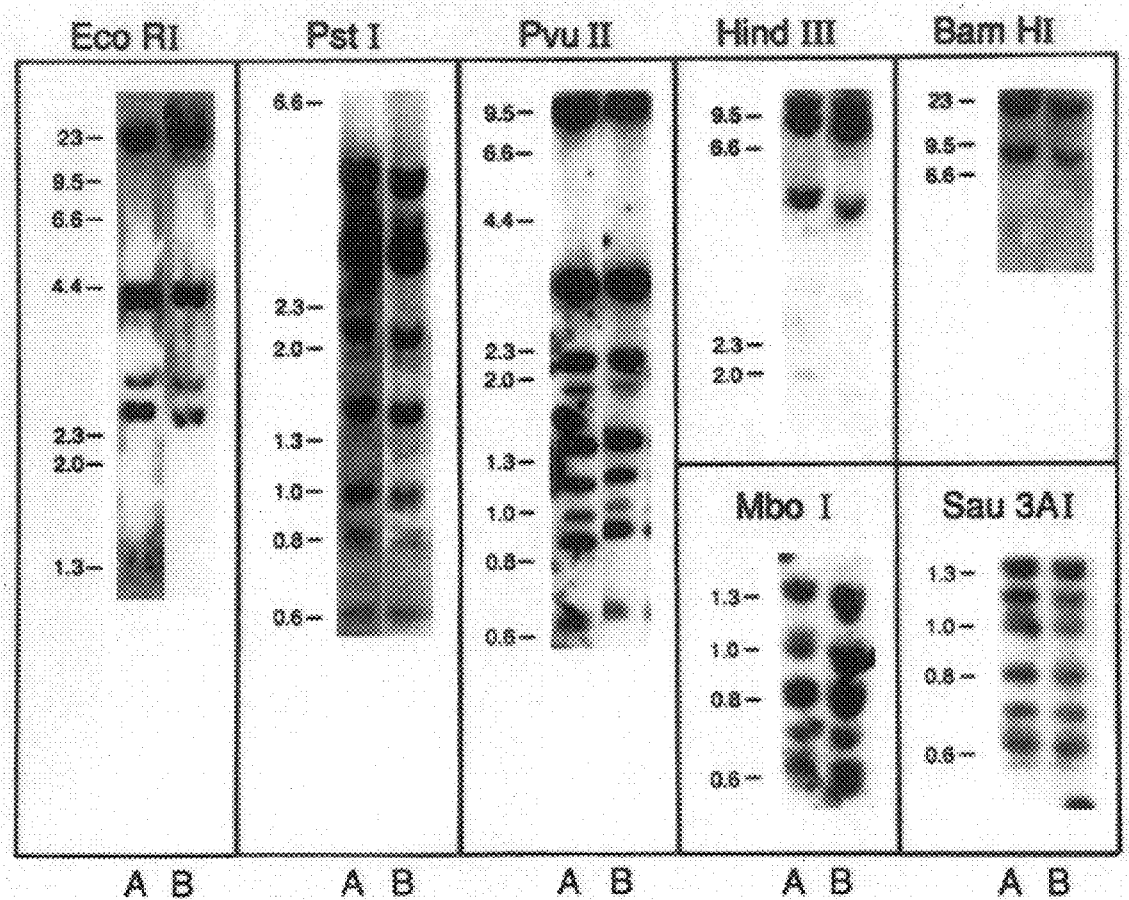
FIG. 3 depicts the restriction fragments produced using DNA from normal samples (A) and from breast cancer cell lines (B), using lactoferrin cDNA (HLF 1212) as a probe. Normal samples (n=2) and DNA from eight cancer lines were digested with indicated enzyme, run in the same gel, and representative lanes cut out for comparison.
Figure 4:
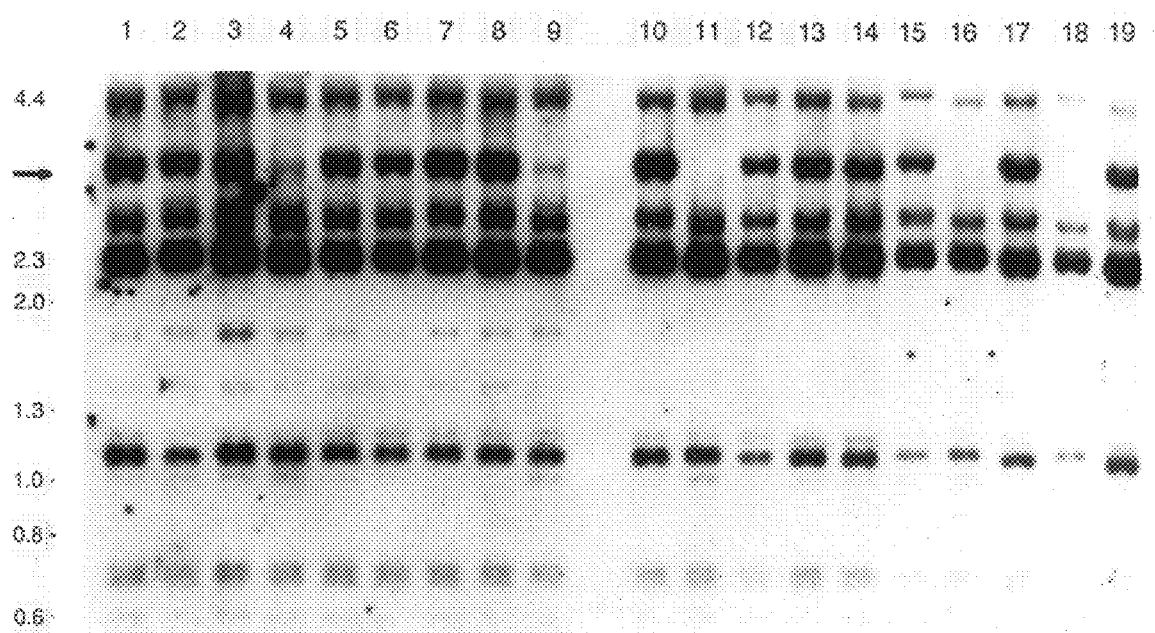
FIG. 4 shows the restriction fragments produced using Msp I and lactoferrin cDNA (HLF 1212) as the probe. Lanes 1–9 are DNA from normal donors. Lanes 10–16 represent DNA from leukemia cells from patients. Lane 17 is cell line K562, lane 18 is KG 1, and lane 19 is U937.
Figure 5:
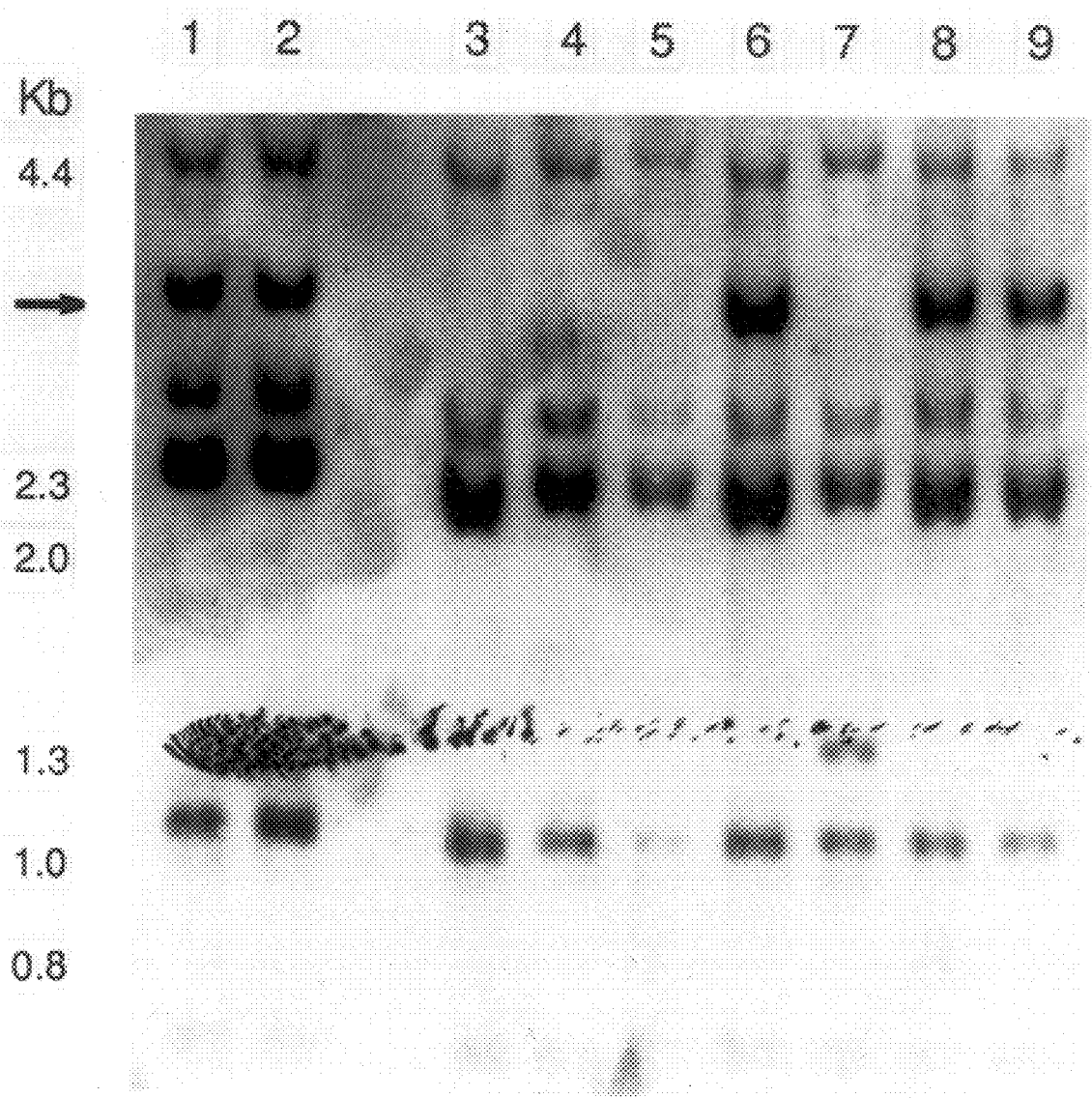
FIG. 5 represents the restriction fragments produced using Msp I and lactoferrin cDNA (HLF 1212) as the probe. Lanes 1 and 2 are DNA from normal donors. Lanes 3–9 represent DNA from breast cancer cell lines. The cell lines are in the following order: Lane 3—MDAMB 468, lane 4—MCF 7, lane 5—BT 474, lane 6—HBL 100, lane 7—MDA 175, lane 8—SKB R3, lane 9—ZR 75-1.

The fragments produced by digestion with Eco RI, Bam HI, Hind III, Pst I, Pvu II, Sau 3AI, or Mbo I, were nearly identical whether the DNA was from normal or malignant cells. The fragment patterns produced by these restriction enzymes in DNA from leukemic and breast cancer cells are shown in FIGS. 2 and 3. Restriction with Msp I indicated the deletion of a 3.5 Kb band in 3 of 10 leukemic cells (FIG. 4), 4 of 7 breast cancer cell lines (FIG. 5), and a much fainter hybridization of this band in 2 of 9 normal specimens (FIG. 4). An extra 1.3 Kb band also occurred in the breast cancer line MDA 175 (FIG. 5, lane 7). There was no relationship between the phenotype or chromosome analysis of the leukemia patients and the Msp I changes.

Figure 6:
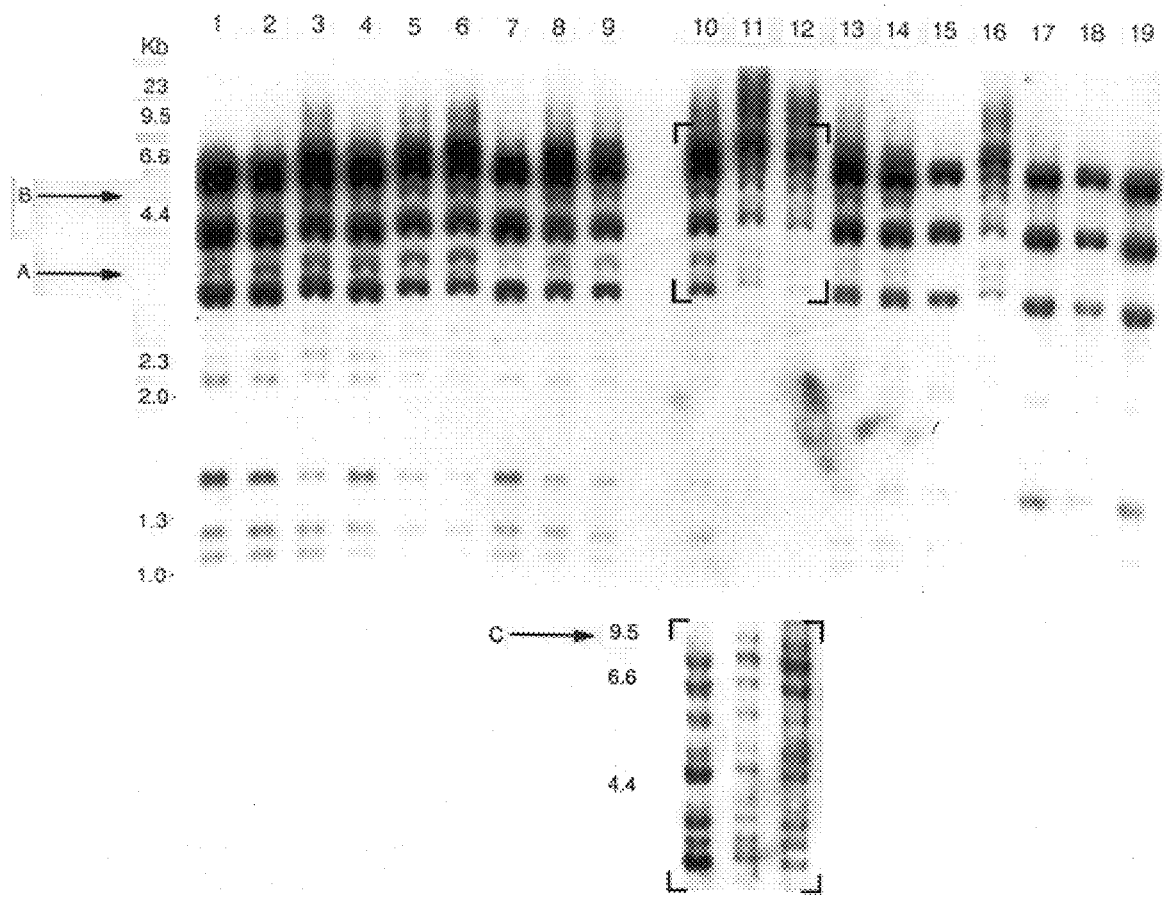
FIG. 6 shows the restriction fragments produced using Xba I and lactoferrin cDNA (HLF 1212) as the probe. Lanes 1–9 are DNA from normal donors. Lanes 10–16 are DNA from leukemia cells from patients and lanes 17–19 DNA from leukemia cell lines (lane 17—K562, lane 18—KG1, lane 19—U937). Arrow A is the band found is patterns A (lanes 1, 2, and 7), B, and C. Arrow B is the band found in patterns B (lanes 3–6, 8–10, 13, 14) and C. Arrow C is only found in pattern C (lanes 11, 12, 16). Insert is the same specimens run on a 0.7% agarose gel.
Figure 7:
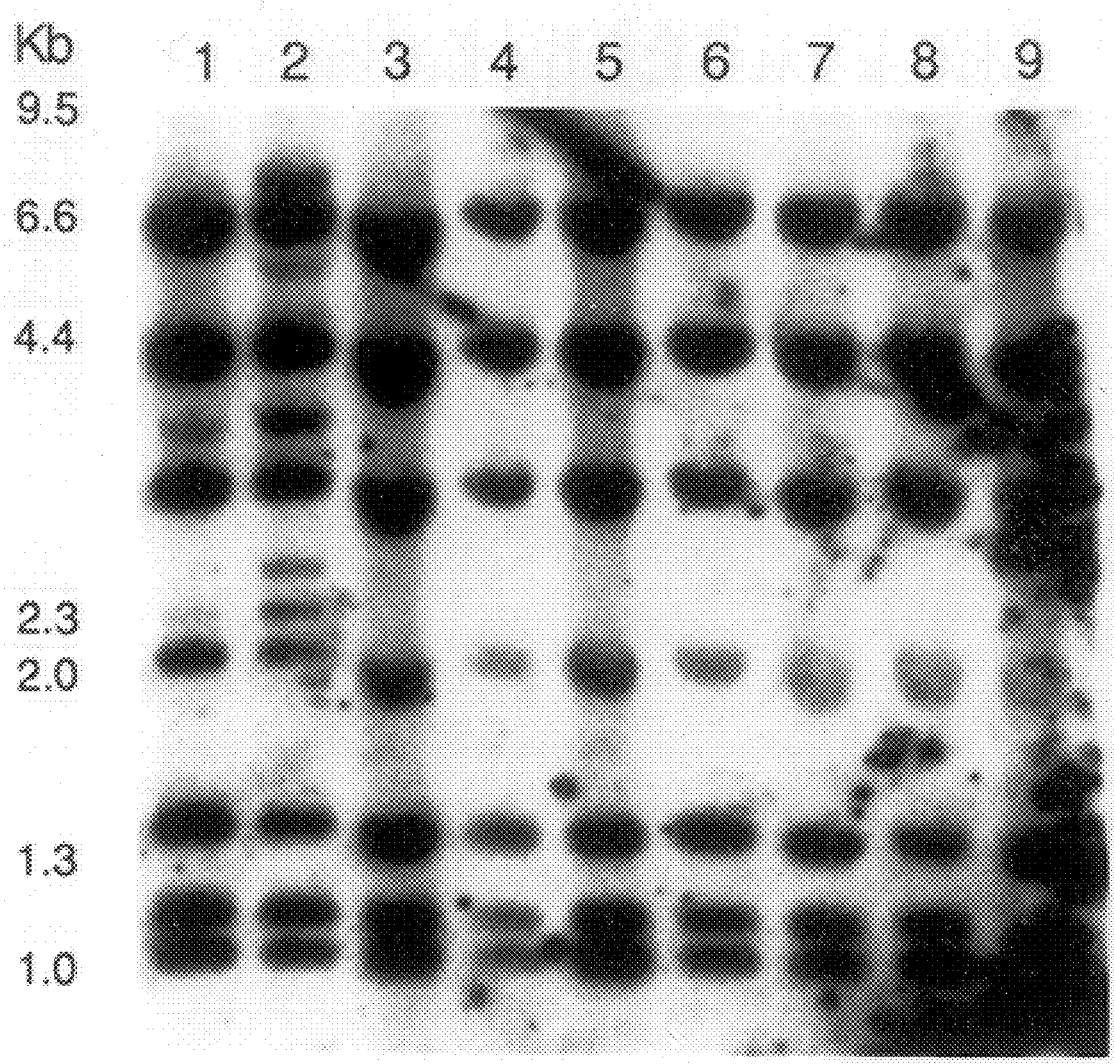
FIG. 7 depicts the restriction fragments produced using Xba I and lactoferrin cDNA (HLF 1212) as the probe. Lanes 1 and 2 are DNA from normal donors. Lanes 3–9 are DNA from breast cancer cell lines. The order is: Lane 3—MDAMB 468, lane 4—BT 474, lane 5—HBL 100, lane 6—MDA 175, lane 7—SKB R3, lane 8—ZR 75-1, lane 9—ZR 75-30. Restriction fragment patterns as discussed in the text are in the following lanes: pattern A is seen in lane 1, pattern B in lane 2, and pattern D in lanes 3–9.
Figure 8:
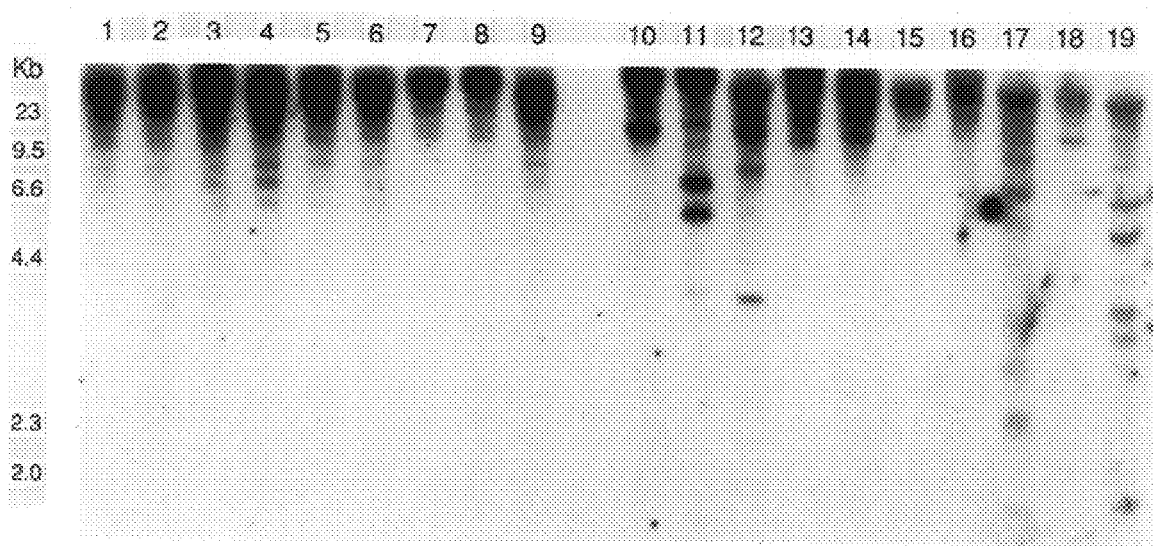
FIG. 8 shows the restriction fragments produced using Hpa II and lactoferrin cDNA (HLF 1212) as the probe. Lanes 1–9 are DNA from normal donors. Lanes 10–16 are DNA from leukemia cells from patients. Lane 17 is cell line KG1, lane 18 is U937, and lane 19 is HL 60.
Figure 9:
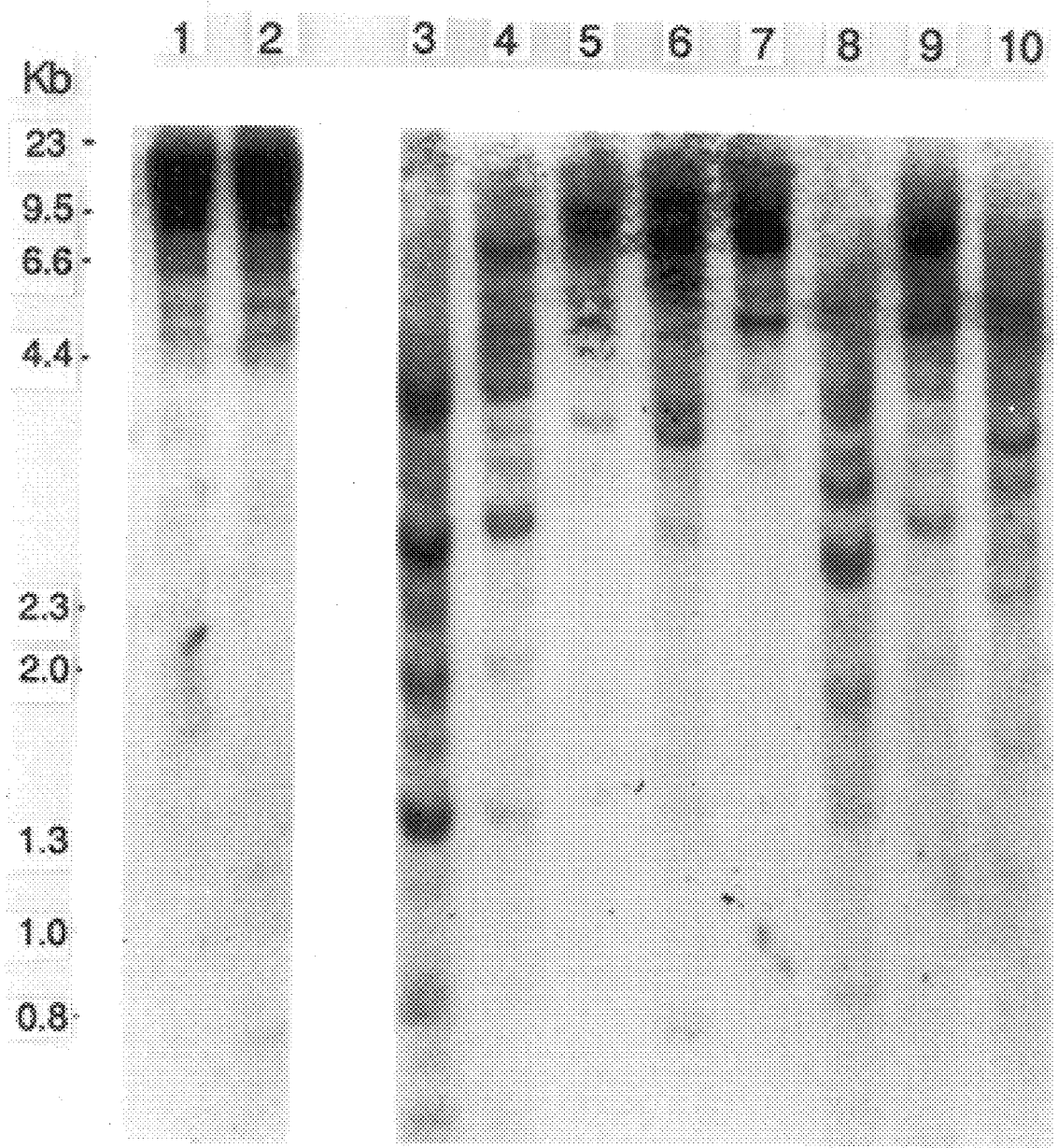
FIG. 9 shows the restriction fragments produced using Hpa II and lactoferrin cDNA (HLF 1212) as the probe. Lanes 1 and 2 are DNA from normal donors. Lanes 3–10 are breast cancer cell lines in the following order: lane 3—MDAMB 468, lane 4—MCF 7, lane 5—BT 474, lane 6—HBL 100, lane 7—MDA 175, lane 8—SKB R3, lane 9—ZR 75-1, lane 10—ZR 75-30.

Fragments produced by Xba I fell into 4 patterns. All patterns contained 4 unchanged bands (~6.5 kb, ~4.2 kb, ~3.0 kb, and ~2.2 kb). Pattern A occurred in 3 of 9 normal samples and contained a 3.5 Kb band and three light <2.0 kb bands in addition to the unchanged bands (FIG. 6, lanes 1, 2, and 7; FIG. 7, lane 1). Pattern B was seen in 6 of 9 normal and 3 of 7 leukemia cells from patients and contained extra 3.5, 5.0, and 6.7 Kb bands along with the three light <2.0 kb bands and the unchanged bands (FIG. 6, lanes 3–6, 8, 9, 10, 13, 14; FIG. 7, lane 2). The last patterns were only seen in DNA obtained from malignant tissue. In pattern C, an extra 9.0 Kb band together with the 3.5, 5.0, and 6.6 kb and unchanged bands were observed in three leukemia patient samples (FIG. 6 lanes 11, 12 (see insert) and lane 16). Also noted is the absence of the light <2.0 kb bands. Pattern D contained only the 4 unchanged and the three light <2.0 kb bands and was present in DNA obtained from all three leukemia and all seven breast cancer cell lines, (FIG. 6, lanes 17–19, and FIG. 7, lanes 3–9). There was one patient (M2 leukemia) with a restriction pattern like that of the cell lines (FIG. 6, lane 15). There were no chromosomal abnormalities, French-American-British (FAB) categories, or phenotypic types associated with any polymorphic Xba I pattern.

Example 4
Isolation and Characterization of the Genomic Lactoferrin Promotor Region.

A human placental DNA library (Clontech) was plated on LE 392 bacterial cells and screened and probed with the 5' end of HLF 1212 (1.3 Kb). Positive clones were cut with SAC 1 and rescreened using a 25 base oligonucleotide (synthesized to match Exon 1 of p1212). All SAC 1 fragments from clone 031A were transformed into Bluescript II KS (stratagene) plasmid. Clone 031A-30 was 2.0 kb and hyridized to Exon 1 oligonucleotide probe. This was sequenced using dideoxynucleotide chain termination and synthesized oligonucleotide primers. Sequence ID NO. 5 shows the sequence of the entire fragment (5'–3') that includes Exon 1.

While the foregoing invention has been described in some detail for purpose of clarity and inderstanding, it will be clear to one skilled in the art from a reading of this diclocure that various changnes in form and detail can be made without departing from the true scope of the invention.

What is claimed is:

1. A method of screening for risk of cancer in a human subject comprising:
   (a) isolating test genomic DNA of a biological sample from tissue that normally expresses lactoferrin and in which abnormal regulation of said lactoferrin is suspected, said tissue being obtained from said subject;
   (b) determining the presence or absence of a polymorphism in said DNA, wherein the presence of said polymorphism indicates a positive correlation with development of cancer, and wherein the step of determining the presence or absence of a polymorphism is carried out by probing or priming said DNA with a human lactoferrin DNA probe or primer;
   wherein said polymorphism is a restriction fragment length polymorphism.

2. A method of screening for risk of cancer in a human subject comprising:
   (a) isolating test aenomic DNA of a biological sample from tissue that normally expresses lactoferrin and in which abnormal regulation of said lactoferrin is suspected, said tissue being obtained from said subject;
   (b) determining the presence or absence of a polymorphism in said DNA, wherein the presence of said polymorphism indicates a positive correlation with development of cancer, and wherein the step of determining the presence or absence of a polymorphism is carried out by probing or priming said DNA with a human lactoferrin DNA probe or primer;
   wherein said probing or priming step comprises:
      (i) digesting said test DNA and normal genomic DNA with a restriction enzyme to obtain restriction fragments;
      (ii) hybridizing the restriction fragments with said lactoferrin DNA probe under conditions such that hybridization is effected to obtain hybridization products; and
      (iii) comparing the hybridization products from said test DNA and said normal DNA to each other.

3. The method of claim 2 wherein said restriction enzyme is Xba I.

4. The method of claim 1 or 2 wherein said biological sample is obtained from leukocytes.

5. The method of claim 1 or 2 wherein said biological sample is obtained from breast cells.

6. The method of claim 1 or 2 wherein said biological sample is obtained from prostate cells.

7. The method of claim 1 or 2 wherein said cancer is leukemia.

8. The method of claim 1 or 2 wherein said cancer is breast cancer.

9. The method of claim 1 or 2 wherein said cancer is prostate cancer.

* * * * *

UNITED STATES PATENT AND TRADEMARK OFFICE
CERTIFICATE OF CORRECTION

PATENT NO. : 5,948,613
DATED : September 7, 1999
INVENTOR(S) : Christina Teng, Timothy J. Panella It is certified that error appears in the above-indentified patent and that said Letters Patent is hereby corrected as shown below:

Column 29, line 43, the word "aenomic" should be corrected to reflect the word "genomic".

Signed and Sealed this

Seventeenth Day of April, 2001

Attest:

NICHOLAS P. GODICI

Attesting Officer    Acting Director of the United States Patent and Trademark Office

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2117 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 1..2117

(xi) SEQUENCE DESCRIPTION: SEQ ID NO:1:

```
CTT GTC TTC CTC GTC CTG CTG TTC CTC GGG GCC CTC GGA CTG TGT CTG        48
Leu Val Phe Leu Val Leu Leu Phe Leu Gly Ala Leu Gly Leu Cys Leu
 1               5                  10                  15

GCT GGC CGT AGG AGA AGG AGT GTT CAG TGG TGC GCC GTA TCC CAA CCC        96
```

-continued

```
            Ala Gly Arg Arg Arg Ser Val Gln Trp Cys Ala Val Ser Gln Pro
                     20              25                  30

GAG GCC ACA AAA TGC TTC CAA TGG CAA AGG AAT ATG AGA AAA GTG CGT      144
Glu Ala Thr Lys Cys Phe Gln Trp Gln Arg Asn Met Arg Lys Val Arg
             35                  40                  45

GGC CCT CCT GTC AGC TGC ATA AAG AGA GAC TCC CCC ATC CAG TGT ATC      192
Gly Pro Pro Val Ser Cys Ile Lys Arg Asp Ser Pro Ile Gln Cys Ile
         50                  55                  60

CAG GCC ATT GCG GAA AAC AGG GCC GAT GCT GTG ACC CTT GAT GGT GGT      240
Gln Ala Ile Ala Glu Asn Arg Ala Asp Ala Val Thr Leu Asp Gly Gly
65                  70                  75                  80

TTC ATA TAC GAG GCA GGC CTG GCC CCC TAC AAA CTG CGA CCT GTA GCG      288
Phe Ile Tyr Glu Ala Gly Leu Ala Pro Tyr Lys Leu Arg Pro Val Ala
                 85                  90                  95

GCG GAA GTC TAC GGG ACC GAA AGA CAG CCA CGA ACT CAC TAT TAT GCC      336
Ala Glu Val Tyr Gly Thr Glu Arg Gln Pro Arg Thr His Tyr Tyr Ala
                100                 105                 110

GTG GCT GTG GTG AAG AAG GGC GGC AGC TTT CAG CTG AAC GAA CTG CAA      384
Val Ala Val Val Lys Lys Gly Gly Ser Phe Gln Leu Asn Glu Leu Gln
            115                 120                 125

GGT CTG AAG TCC TGC CAC ACA GGC CTT CGC AGG ACC GCT GGA TGG AAT      432
Gly Leu Lys Ser Cys His Thr Gly Leu Arg Arg Thr Ala Gly Trp Asn
        130                 135                 140

GTC CCT ATA GGG ACA CTT CGT CCA TTC TTG AAT TGG ACG GGT CCA CCT      480
Val Pro Ile Gly Thr Leu Arg Pro Phe Leu Asn Trp Thr Gly Pro Pro
145                 150                 155                 160

GAG CCC ATT GAG GCA GCT GTG GCC AGG TTC TTC TCA GCC AGC TGT GTT      528
Glu Pro Ile Glu Ala Ala Val Ala Arg Phe Phe Ser Ala Ser Cys Val
                165                 170                 175

CCC GGT GCA GAT AAA GGA CAG TTC CCC AAC CTG TGT CGC CTG TGT GCG      576
Pro Gly Ala Asp Lys Gly Gln Phe Pro Asn Leu Cys Arg Leu Cys Ala
            180                 185                 190

GGG ACA GGG GAA AAC AAA TGT GCC TTC TCC TCC CAG GAA CCG TAC TTC      624
Gly Thr Gly Glu Asn Lys Cys Ala Phe Ser Ser Gln Glu Pro Tyr Phe
        195                 200                 205

AGC TAC TCT GGT GCC TTC AAG TGT CTG AGA GAC GGG GCT GGA GAC GTG      672
Ser Tyr Ser Gly Ala Phe Lys Cys Leu Arg Asp Gly Ala Gly Asp Val
210                 215                 220

GCT TTT ATC AGA GAG AGC ACA GTG TTT GAG GAC CTG TCA GAC GAG GCT      720
Ala Phe Ile Arg Glu Ser Thr Val Phe Glu Asp Leu Ser Asp Glu Ala
225                 230                 235                 240

GAA AGG GAC GAG TAT GAG TTA CTC TGC CCA GAC AAC ACT CGG AAG CCA      768
Glu Arg Asp Glu Tyr Glu Leu Leu Cys Pro Asp Asn Thr Arg Lys Pro
                245                 250                 255

GTG GAC AAG TTC AAA GAC TGC CAT CTG GCC CGG GTC CCT TCT CAT GCC      816
Val Asp Lys Phe Lys Asp Cys His Leu Ala Arg Val Pro Ser His Ala
            260                 265                 270

GTT GTG GCA CGA AGT GTG AAT GGC AAG GAG GAT GCC ATC TGG AAT CTT      864
Val Val Ala Arg Ser Val Asn Gly Lys Glu Asp Ala Ile Trp Asn Leu
        275                 280                 285

CTC CGC CAG GCA CAG GAA AAG TTT GGA AAG GAC AAG TCA CCG AAA TTC      912
Leu Arg Gln Ala Gln Glu Lys Phe Gly Lys Asp Lys Ser Pro Lys Phe
            290                 295                 300

CAG CTC TTT GGC TCC CCT AGT GGG CAG AAA GAT CTG CTG TTC AAG GAC      960
Gln Leu Phe Gly Ser Pro Ser Gly Gln Lys Asp Leu Leu Phe Lys Asp
305                 310                 315                 320

TCT GCC ATT GGG TTT TCG AGG GTG CCC CCG AGG ATA GAT TCT GGG CTG     1008
Ser Ala Ile Gly Phe Ser Arg Val Pro Pro Arg Ile Asp Ser Gly Leu
                325                 330                 335

TAC CTT GGC TCC GGC TAC TTC ACT GCC ATC CAG AAC TTG AGG AAA AGT     1056
```

-continued

| | |
|---|---|
| Tyr Leu Gly Ser Gly Tyr Phe Thr Ala Ile Gln Asn Leu Arg Lys Ser<br>340 345 350 | |
| GAG GAG GAA GTG GCT GCC CGG CGT GCG CGG GTC GTG TGG TGT GCG GTG<br>Glu Glu Glu Val Ala Ala Arg Arg Ala Arg Val Val Trp Cys Ala Val<br>355 360 365 | 1104 |
| GGC GAG CAG GAG CTG CGC AAG TGT AAC CAG TGG AGT GGC TTG AGC GAA<br>Gly Glu Gln Glu Leu Arg Lys Cys Asn Gln Trp Ser Gly Leu Ser Glu<br>370 375 380 | 1152 |
| GGC AGC GTG ACC TGC TCC TCG GCC TCC ACC ACA GAG GAC TGC ATC GCC<br>Gly Ser Val Thr Cys Ser Ser Ala Ser Thr Thr Glu Asp Cys Ile Ala<br>385 390 395 400 | 1200 |
| CTG GTG CTG AAA GGA GAA GCT GAT GCC ATG AGT TTG GAT GGA GGA TAT<br>Leu Val Leu Lys Gly Glu Ala Asp Ala Met Ser Leu Asp Gly Gly Tyr<br>405 410 415 | 1248 |
| GTG TAC ACT GCA GGC AAA TGT GGT TTG GTG CCT GTC CTG GCA GAG AAC<br>Val Tyr Thr Ala Gly Lys Cys Gly Leu Val Pro Val Leu Ala Glu Asn<br>420 425 430 | 1296 |
| TAC AAA TCC CAA CAA AGC AGT GAC CCT GAT CCT AAC TGT GTG GAT AGA<br>Tyr Lys Ser Gln Gln Ser Ser Asp Pro Asp Pro Asn Cys Val Asp Arg<br>435 440 445 | 1344 |
| CCT GTG GAA GGA TAT CTT GCT GTG GCG GTG GTT AGG AGA TCA GAC ACT<br>Pro Val Glu Gly Tyr Leu Ala Val Ala Val Val Arg Arg Ser Asp Thr<br>450 455 460 | 1392 |
| AGC CTT ACC TGG AAC TCT GTG AAA GGC AAG AAG TCC TGC CAC ACC GCC<br>Ser Leu Thr Trp Asn Ser Val Lys Gly Lys Lys Ser Cys His Thr Ala<br>465 470 475 480 | 1440 |
| GTG GAC AGG ACT GCA GGC TGG AAT ATC CCC ATG GGC CTG CTC TTC AAC<br>Val Asp Arg Thr Ala Gly Trp Asn Ile Pro Met Gly Leu Leu Phe Asn<br>485 490 495 | 1488 |
| CAG ACG GGC TCC TGC AAA TTT GAT GAA TAT TTC AGT CAA AGC TGT GCC<br>Gln Thr Gly Ser Cys Lys Phe Asp Glu Tyr Phe Ser Gln Ser Cys Ala<br>500 505 510 | 1536 |
| CCT GGG TCT GAC CCG AGA TCT AAT CTC TGT GCT CTG TGT ATT GGC GAC<br>Pro Gly Ser Asp Pro Arg Ser Asn Leu Cys Ala Leu Cys Ile Gly Asp<br>515 520 525 | 1584 |
| GAG CAG GGT GAG AAT AAG TGC GTG CCC AAC AGC AAC GAG AGA TAC TAC<br>Glu Gln Gly Glu Asn Lys Cys Val Pro Asn Ser Asn Glu Arg Tyr Tyr<br>530 535 540 | 1632 |
| GGC TAC ACT GGG GCT TTC CGG TGC CTG GCT GAG AAT GCT GGA GAC GTT<br>Gly Tyr Thr Gly Ala Phe Arg Cys Leu Ala Glu Asn Ala Gly Asp Val<br>545 550 555 560 | 1680 |
| GCA TTT GTG AAA GAT GTC ACT GTC TTG CAG AAC ACT GAT GGA AAT AAC<br>Ala Phe Val Lys Asp Val Thr Val Leu Gln Asn Thr Asp Gly Asn Asn<br>565 570 575 | 1728 |
| AAT GAG GCA TGG GCT AAG GAT TTG AAG CTG GCA GAC TTT GCG CTG CTG<br>Asn Glu Ala Trp Ala Lys Asp Leu Lys Leu Ala Asp Phe Ala Leu Leu<br>580 585 590 | 1776 |
| TGC CTC GAT GGC AAA CGG AAG CCT GTG ACT GAG GCT AGA AGC TGC CAT<br>Cys Leu Asp Gly Lys Arg Lys Pro Val Thr Glu Ala Arg Ser Cys His<br>595 600 605 | 1824 |
| CTT GCC ATG GCC CCG AAT CAT GCC GTG GTG TCT CGG ATG GAT AAG GTG<br>Leu Ala Met Ala Pro Asn His Ala Val Val Ser Arg Met Asp Lys Val<br>610 615 620 | 1872 |
| GAA CGC CTG AAA CAG GTG TTG CTC CAC CAA CAG GCT AAA TTT GGG AGA<br>Glu Arg Leu Lys Gln Val Leu Leu His Gln Gln Ala Lys Phe Gly Arg<br>625 630 635 640 | 1920 |
| AAT GGA TCT GAC TGC CCG GAC AAG TTT TGC TTA TTC CAG TCT GAA ACC<br>Asn Gly Ser Asp Cys Pro Asp Lys Phe Cys Leu Phe Gln Ser Glu Thr<br>645 650 655 | 1968 |
| AAA AAC CTT CTG TTC AAT GAC AAC ACT GAG TGT CTG GCC AGA CTC CAT | 2016 |

```
Lys Asn Leu Leu Phe Asn Asp Asn Thr Glu Cys Leu Ala Arg Leu His
            660                 665                 670

GGC AAA ACA ACA TAT GAA AAA TAT TTG GGA CCA CAG TAT GTC GCA GGC        2064
Gly Lys Thr Thr Tyr Glu Lys Tyr Leu Gly Pro Gln Tyr Val Ala Gly
        675                 680                 685

ATT ACT AAT CTG AAA AAG TGC TCA ACC TCC CCC TCC TGG AAG CCT GTG        2112
Ile Thr Asn Leu Lys Lys Cys Ser Thr Ser Pro Ser Trp Lys Pro Val
690                 695                 700

AAT TC                                                                  2117
Asn
705

(2) INFORMATION FOR SEQ ID NO:2:

(i) SEQUENCE CHARACTERISTICS:
        (A) LENGTH: 705 amino acids
        (B) TYPE: amino acid
        (D) TOPOLOGY: linear (ii) MOLECULE TYPE: protein (xi) SEQUENCE DESCRIPTION: SEQ ID NO:2:

Leu Val Phe Leu Val Leu Leu Phe Leu Gly Ala Leu Gly Leu Cys Leu
1               5                   10                  15

Ala Gly Arg Arg Arg Ser Val Gln Trp Cys Ala Val Ser Gln Pro
        20                  25                  30

Glu Ala Thr Lys Cys Phe Gln Trp Gln Arg Asn Met Arg Lys Val Arg
        35                  40                  45

Gly Pro Pro Val Ser Cys Ile Lys Arg Asp Ser Pro Ile Gln Cys Ile
        50                  55                  60

Gln Ala Ile Ala Glu Asn Arg Ala Asp Ala Val Thr Leu Asp Gly Gly
65                  70                  75                  80

Phe Ile Tyr Glu Ala Gly Leu Ala Pro Tyr Lys Leu Arg Pro Val Ala
                85                  90                  95

Ala Glu Val Tyr Gly Thr Glu Arg Gln Pro Arg Thr His Tyr Tyr Ala
                100                 105                 110

Val Ala Val Val Lys Lys Gly Gly Ser Phe Gln Leu Asn Glu Leu Gln
            115                 120                 125

Gly Leu Lys Ser Cys His Thr Gly Leu Arg Arg Thr Ala Gly Trp Asn
130                 135                 140

Val Pro Ile Gly Thr Leu Arg Pro Phe Leu Asn Trp Thr Gly Pro Pro
145                 150                 155                 160

Glu Pro Ile Glu Ala Ala Val Ala Arg Phe Phe Ser Ala Ser Cys Val
                165                 170                 175

Pro Gly Ala Asp Lys Gly Gln Phe Pro Asn Leu Cys Arg Leu Cys Ala
                180                 185                 190

Gly Thr Gly Glu Asn Lys Cys Ala Phe Ser Ser Gln Glu Pro Tyr Phe
            195                 200                 205

Ser Tyr Ser Gly Ala Phe Lys Cys Leu Arg Asp Gly Ala Gly Asp Val
        210                 215                 220

Ala Phe Ile Arg Glu Ser Thr Val Phe Glu Asp Leu Ser Asp Glu Ala
225                 230                 235                 240

Glu Arg Asp Glu Tyr Glu Leu Leu Cys Pro Asp Asn Thr Arg Lys Pro
                245                 250                 255

Val Asp Lys Phe Lys Asp Cys His Leu Ala Arg Val Pro Ser His Ala
                260                 265                 270

Val Val Ala Arg Ser Val Asn Gly Lys Glu Asp Ala Ile Trp Asn Leu
            275                 280                 285
```

-continued

```
Leu Arg Gln Ala Gln Glu Lys Phe Gly Lys Asp Lys Ser Pro Lys Phe
        290                 295                 300
Gln Leu Phe Gly Ser Pro Ser Gly Gln Lys Asp Leu Leu Phe Lys Asp
305                 310                 315                 320
Ser Ala Ile Gly Phe Ser Arg Val Pro Arg Ile Asp Ser Gly Leu
                325                 330                 335
Tyr Leu Gly Ser Gly Tyr Phe Thr Ala Ile Gln Asn Leu Arg Lys Ser
                340                 345                 350
Glu Glu Glu Val Ala Ala Arg Arg Ala Arg Val Val Trp Cys Ala Val
            355                 360                 365
Gly Glu Gln Glu Leu Arg Lys Cys Asn Gln Trp Ser Gly Leu Ser Glu
        370                 375                 380
Gly Ser Val Thr Cys Ser Ser Ala Ser Thr Thr Glu Asp Cys Ile Ala
385                 390                 395                 400
Leu Val Leu Lys Gly Glu Ala Asp Ala Met Ser Leu Asp Gly Gly Tyr
                405                 410                 415
Val Tyr Thr Ala Gly Lys Cys Gly Leu Val Pro Val Leu Ala Glu Asn
                420                 425                 430
Tyr Lys Ser Gln Gln Ser Ser Asp Pro Asp Pro Asn Cys Val Asp Arg
            435                 440                 445
Pro Val Glu Gly Tyr Leu Ala Val Ala Val Val Arg Arg Ser Asp Thr
        450                 455                 460
Ser Leu Thr Trp Asn Ser Val Lys Gly Lys Lys Ser Cys His Thr Ala
465                 470                 475                 480
Val Asp Arg Thr Ala Gly Trp Asn Ile Pro Met Gly Leu Leu Phe Asn
                485                 490                 495
Gln Thr Gly Ser Cys Lys Phe Asp Glu Tyr Phe Ser Gln Ser Cys Ala
                500                 505                 510
Pro Gly Ser Asp Pro Arg Ser Asn Leu Cys Ala Leu Cys Ile Gly Asp
            515                 520                 525
Glu Gln Gly Glu Asn Lys Cys Val Pro Asn Ser Asn Glu Arg Tyr Tyr
        530                 535                 540
Gly Tyr Thr Gly Ala Phe Arg Cys Leu Ala Glu Asn Ala Gly Asp Val
545                 550                 555                 560
Ala Phe Val Lys Asp Val Thr Val Leu Gln Asn Thr Asp Gly Asn Asn
                565                 570                 575
Asn Glu Ala Trp Ala Lys Asp Leu Lys Leu Ala Asp Phe Ala Leu Leu
                580                 585                 590
Cys Leu Asp Gly Lys Arg Lys Pro Val Thr Glu Ala Arg Ser Cys His
            595                 600                 605
Leu Ala Met Ala Pro Asn His Ala Val Val Ser Arg Met Asp Lys Val
        610                 615                 620
Glu Arg Leu Lys Gln Val Leu Leu His Gln Gln Ala Lys Phe Gly Arg
625                 630                 635                 640
Asn Gly Ser Asp Cys Pro Asp Lys Phe Cys Leu Phe Gln Ser Glu Thr
                645                 650                 655
Lys Asn Leu Leu Phe Asn Asp Asn Thr Glu Cys Leu Ala Arg Leu His
                660                 665                 670
Gly Lys Thr Thr Tyr Glu Lys Tyr Leu Gly Pro Gln Tyr Val Ala Gly
            675                 680                 685
Ile Thr Asn Leu Lys Lys Cys Ser Thr Ser Pro Ser Trp Lys Pro Val
        690                 695                 700
Asn
```

-continued (2) INFORMATION FOR SEQ ID NO:3:

(i) SEQUENCE CHARACTERISTICS:
        (A) LENGTH: 2124 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..2124

(xi) SEQUENCE DESCRIPTION: SEQ ID NO:3:

```
ATG AAA CTT GTC TTC CTC GTC CTG CTG TTC CTC GGG GCC CTC GGA CTG        48
Met Lys Leu Val Phe Leu Val Leu Leu Phe Leu Gly Ala Leu Gly Leu
 1               5                  10                  15

TGT CTG GCT GGC CGT AGG AGA AGG AGT GTT CAG TGG TGC GCC GTA TCC        96
Cys Leu Ala Gly Arg Arg Arg Arg Ser Val Gln Trp Cys Ala Val Ser
             20                  25                  30

CAA CCC GAG GCC ACA AAA TGC TTC CAA TGG CAA AGG AAT ATG AGA AAA       144
Gln Pro Glu Ala Thr Lys Cys Phe Gln Trp Gln Arg Asn Met Arg Lys
         35                  40                  45

GTG CGT GGC CCT CCT GTC AGC TGC ATA AAG AGA GAC TCC CCC ATC CAG       192
Val Arg Gly Pro Pro Val Ser Cys Ile Lys Arg Asp Ser Pro Ile Gln
 50                  55                  60

TGT ATC CAG GCC ATT GCG GAA AAC AGG GCC GAT GCT GTG ACC CTT GAT       240
Cys Ile Gln Ala Ile Ala Glu Asn Arg Ala Asp Ala Val Thr Leu Asp
 65                  70                  75                  80

GGT GGT TTC ATA TAC GAG GCA GGC CTG GCC CCC TAC AAA CTG CGA CCT       288
Gly Gly Phe Ile Tyr Glu Ala Gly Leu Ala Pro Tyr Lys Leu Arg Pro
                 85                  90                  95

GTA GCG GCG GAA GTC TAC GGG ACC GAA AGA CAG CCA CGA ACT CAC TAT       336
Val Ala Ala Glu Val Tyr Gly Thr Glu Arg Gln Pro Arg Thr His Tyr
            100                 105                 110

TAT GCC GTG GCT GTG GTG AAG AAG GGC GGC AGC TTT CAG CTG AAC GAA       384
Tyr Ala Val Ala Val Val Lys Lys Gly Gly Ser Phe Gln Leu Asn Glu
        115                 120                 125

CTG CAA GGT CTG AAG TCC TGC CAC ACA GGC CTT CGC AGG ACC GCT GGA       432
Leu Gln Gly Leu Lys Ser Cys His Thr Gly Leu Arg Arg Thr Ala Gly
130                 135                 140

TGG AAT GTC CCT ATA GGG ACA CTT CGT CCA TTC TTG AAT TGG ACG GGT       480
Trp Asn Val Pro Ile Gly Thr Leu Arg Pro Phe Leu Asn Trp Thr Gly
145                 150                 155                 160

CCA CCT GAG CCC ATT GAG GCA GCT GTG GCC AGG TTC TTC TCA GCC AGC       528
Pro Pro Glu Pro Ile Glu Ala Ala Val Ala Arg Phe Phe Ser Ala Ser
                165                 170                 175

TGT GTT CCC GGT GCA GAT AAA GGA CAG TTC CCC AAC CTG TGT CGC CTG       576
Cys Val Pro Gly Ala Asp Lys Gly Gln Phe Pro Asn Leu Cys Arg Leu
            180                 185                 190

TGT GCG GGG ACA GGG GAA AAC AAA TGT GCC TTC TCC TCC CAG GAA CCG       624
Cys Ala Gly Thr Gly Glu Asn Lys Cys Ala Phe Ser Ser Gln Glu Pro
        195                 200                 205

TAC TTC AGC TAC TCT GGT GCC TTC AAG TGT CTG AGA GAC GGG GCT GGA       672
Tyr Phe Ser Tyr Ser Gly Ala Phe Lys Cys Leu Arg Asp Gly Ala Gly
    210                 215                 220

GAC GTG GCT TTT ATC AGA GAG AGC ACA GTG TTT GAG GAC CTG TCA GAC       720
Asp Val Ala Phe Ile Arg Glu Ser Thr Val Phe Glu Asp Leu Ser Asp
225                 230                 235                 240

GAG GCT GAA AGG GAC GAG TAT GAG TTA CTC TGC CCA GAC AAC ACT CGG       768
Glu Ala Glu Arg Asp Glu Tyr Glu Leu Leu Cys Pro Asp Asn Thr Arg
                245                 250                 255
```

-continued

| | |
|---|---|
| AAG CCA GTG GAC AAG TTC AAA GAC TGC CAT CTG GCC CGG GTC CCT TCT<br>Lys Pro Val Asp Lys Phe Lys Asp Cys His Leu Ala Arg Val Pro Ser<br>          260                     265                   270 | 816 |
| CAT GCC GTT GTG GCA CGA AGT GTG AAT GGC AAG GAG GAT GCC ATC TGG<br>His Ala Val Val Ala Arg Ser Val Asn Gly Lys Glu Asp Ala Ile Trp<br>                 275                    280                   285 | 864 |
| AAT CTT CTC CGC CAG GCA CAG GAA AAG TTT GGA AAG GAC AAG TCA CCG<br>Asn Leu Leu Arg Gln Ala Gln Glu Lys Phe Gly Lys Asp Lys Ser Pro<br>290                     295                    300 | 912 |
| AAA TTC CAG CTC TTT GGC TCC CCT AGT GGG CAG AAA GAT CTG CTG TTC<br>Lys Phe Gln Leu Phe Gly Ser Pro Ser Gly Gln Lys Asp Leu Leu Phe<br>305                   310                   315               320 | 960 |
| AAG GAC TCT GCC ATT GGG TTT TCG AGG GTG CCC CCG AGG ATA GAT TCT<br>Lys Asp Ser Ala Ile Gly Phe Ser Arg Val Pro Pro Arg Ile Asp Ser<br>               325                    330                   335 | 1008 |
| GGG CTG TAC CTT GGC TCC GGC TAC TTC ACT GCC ATC CAG AAC TTG AGG<br>Gly Leu Tyr Leu Gly Ser Gly Tyr Phe Thr Ala Ile Gln Asn Leu Arg<br>             340                    345                   350 | 1056 |
| AAA AGT GAG GAG GAA GTG GCT GCC CGG CGT GCG CGG GTC GTG TGG TGT<br>Lys Ser Glu Glu Glu Val Ala Ala Arg Arg Ala Arg Val Val Trp Cys<br>          355                    360                   365 | 1104 |
| GCG GTG GGC GAG CAG GAG CTG CGC AAG TGT AAC CAG TGG AGT GGC TTG<br>Ala Val Gly Glu Gln Glu Leu Arg Lys Cys Asn Gln Trp Ser Gly Leu<br>370                     375                    380 | 1152 |
| AGC GAA GGC AGC GTG ACC TGC TCC TCG GCC TCC ACC ACA GAG GAC TGC<br>Ser Glu Gly Ser Val Thr Cys Ser Ser Ala Ser Thr Thr Glu Asp Cys<br>385                   390                   395               400 | 1200 |
| ATC GCC CTG GTG CTG AAA GGA GAA GCT GAT GCC ATG AGT TTG GAT GGA<br>Ile Ala Leu Val Leu Lys Gly Glu Ala Asp Ala Met Ser Leu Asp Gly<br>                   405                    410                   415 | 1248 |
| GGA TAT GTG TAC ACT GCA GGC AAA TGT GGT TTG GTG CCT GTC CTG GCA<br>Gly Tyr Val Tyr Thr Ala Gly Lys Cys Gly Leu Val Pro Val Leu Ala<br>             420                    425                   430 | 1296 |
| GAG AAC TAC AAA TCC CAA CAA AGC AGT GAC CCT GAT CCT AAC TGT GTG<br>Glu Asn Tyr Lys Ser Gln Gln Ser Ser Asp Pro Asp Pro Asn Cys Val<br>          435                    440                   445 | 1344 |
| GAT AGA CCT GTG GAA GGA TAT CTT GCT GTG GCG GTG GTT AGG AGA TCA<br>Asp Arg Pro Val Glu Gly Tyr Leu Ala Val Ala Val Val Arg Arg Ser<br>450                     455                    460 | 1392 |
| GAC ACT AGC CTT ACC TGG AAC TCT GTG AAA GGC AAG AAG TCC TGC CAC<br>Asp Thr Ser Leu Thr Trp Asn Ser Val Lys Gly Lys Lys Ser Cys His<br>465                   470                   475               480 | 1440 |
| ACC GCC GTG GAC AGG ACT GCA GGC TGG AAT ATC CCC ATG GGC CTG CTC<br>Thr Ala Val Asp Arg Thr Ala Gly Trp Asn Ile Pro Met Gly Leu Leu<br>                   485                    490                   495 | 1488 |
| TTC AAC CAG ACG GGC TCC TGC AAA TTT GAT GAA TAT TTC AGT CAA AGC<br>Phe Asn Gln Thr Gly Ser Cys Lys Phe Asp Glu Tyr Phe Ser Gln Ser<br>             500                    505                   510 | 1536 |
| TGT GCC CCT GGG TCT GAC CCG AGA TCT AAT CTC TGT GCT CTG TGT ATT<br>Cys Ala Pro Gly Ser Asp Pro Arg Ser Asn Leu Cys Ala Leu Cys Ile<br>          515                    520                   525 | 1584 |
| GGC GAC GAG CAG GGT GAG AAT AAG TGC GTG CCC AAC AGC AAC GAG AGA<br>Gly Asp Glu Gln Gly Glu Asn Lys Cys Val Pro Asn Ser Asn Glu Arg<br>530                     535                    540 | 1632 |
| TAC TAC GGC TAC ACT GGG GCT TTC CGG TGC CTG GCT GAG AAT GCT GGA<br>Tyr Tyr Gly Tyr Thr Gly Ala Phe Arg Cys Leu Ala Glu Asn Ala Gly<br>545                   550                   555               560 | 1680 |
| GAC GTT GCA TTT GTG AAA GAT GTC ACT GTC TTG CAG AAC ACT GAT GGA<br>Asp Val Ala Phe Val Lys Asp Val Thr Val Leu Gln Asn Thr Asp Gly<br>               565                    570                   575 | 1728 |

```
AAT AAC AAT GAG GCA TGG GCT AAG GAT TTG AAG CTG GCA GAC TTT GCG      1776
Asn Asn Asn Glu Ala Trp Ala Lys Asp Leu Lys Leu Ala Asp Phe Ala
            580                 585                 590

CTG CTG TGC CTC GAT GGC AAA CGG AAG CCT GTG ACT GAG GCT AGA AGC      1824
Leu Leu Cys Leu Asp Gly Lys Arg Lys Pro Val Thr Glu Ala Arg Ser
            595                 600                 605

TGC CAT CTT GCC ATG GCC CCG AAT CAT GCC GTG GTG TCT CGG ATG GAT      1872
Cys His Leu Ala Met Ala Pro Asn His Ala Val Val Ser Arg Met Asp
610                 615                 620

AAG GTG GAA CGC CTG AAA CAG GTG TTG CTC CAC CAA CAG GCT AAA TTT      1920
Lys Val Glu Arg Leu Lys Gln Val Leu Leu His Gln Gln Ala Lys Phe
625                 630                 635                 640

GGG AGA AAT GGA TCT GAC TGC CCG GAC AAG TTT TGC TTA TTC CAG TCT      1968
Gly Arg Asn Gly Ser Asp Cys Pro Asp Lys Phe Cys Leu Phe Gln Ser
                645                 650                 655

GAA ACC AAA AAC CTT CTG TTC AAT GAC AAC ACT GAG TGT CTG GCC AGA      2016
Glu Thr Lys Asn Leu Leu Phe Asn Asp Asn Thr Glu Cys Leu Ala Arg
            660                 665                 670

CTC CAT GGC AAA ACA ACA TAT GAA AAA TAT TTG GGA CCA CAG TAT GTC      2064
Leu His Gly Lys Thr Thr Tyr Glu Lys Tyr Leu Gly Pro Gln Tyr Val
            675                 680                 685

GCA GGC ATT ACT AAT CTG AAA AAG TGC TCA ACC TCC CCC CTC CTG GAA      2112
Ala Gly Ile Thr Asn Leu Lys Lys Cys Ser Thr Ser Pro Leu Leu Glu
690                 695                 700

GCC TGT GAA TTC                                                       2124
Ala Cys Glu Phe
705

(2) INFORMATION FOR SEQ ID NO:4:

(i) SEQUENCE CHARACTERISTICS:
        (A) LENGTH: 708 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
```

-continued

```
                   165                 170                 175
Cys Val Pro Gly Ala Asp Lys Gly Gln Phe Pro Asn Leu Cys Arg Leu
                180                 185                 190
Cys Ala Gly Thr Gly Glu Asn Lys Cys Ala Phe Ser Ser Gln Glu Pro
            195                 200                 205
Tyr Phe Ser Tyr Ser Gly Ala Phe Lys Cys Leu Arg Asp Gly Ala Gly
        210                 215                 220
Asp Val Ala Phe Ile Arg Glu Ser Thr Val Phe Glu Asp Leu Ser Asp
225                 230                 235                 240
Glu Ala Glu Arg Asp Glu Tyr Glu Leu Leu Cys Pro Asp Asn Thr Arg
                245                 250                 255
Lys Pro Val Asp Lys Phe Lys Asp Cys His Leu Ala Arg Val Pro Ser
                260                 265                 270
His Ala Val Val Ala Arg Ser Val Asn Gly Lys Glu Asp Ala Ile Trp
            275                 280                 285
Asn Leu Leu Arg Gln Ala Gln Glu Lys Phe Gly Lys Asp Lys Ser Pro
        290                 295                 300
Lys Phe Gln Leu Phe Gly Ser Pro Ser Gly Gln Lys Asp Leu Leu Phe
305                 310                 315                 320
Lys Asp Ser Ala Ile Gly Phe Ser Arg Val Pro Pro Arg Ile Asp Ser
                325                 330                 335
Gly Leu Tyr Leu Gly Ser Gly Tyr Phe Thr Ala Ile Gln Asn Leu Arg
                340                 345                 350
Lys Ser Glu Glu Glu Val Ala Ala Arg Arg Ala Arg Val Val Trp Cys
            355                 360                 365
Ala Val Gly Glu Gln Glu Leu Arg Lys Cys Asn Gln Trp Ser Gly Leu
        370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Gly Lys Cys Gly Leu Val Pro Val Leu Ala
                420                 425                 430
Glu Asn Tyr Lys Ser Gln Gln Ser Ser Asp Pro Asp Pro Asn Cys Val
            435                 440                 445
Asp Arg Pro Val Glu Gly Tyr Leu Ala Val Ala Val Val Arg Arg Ser
        450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
                500                 505                 510
Cys Ala Pro Gly Ser Asp Pro Arg Ser Asn Leu Cys Ala Leu Cys Ile
            515                 520                 525
Gly Asp Glu Gln Gly Glu Asn Lys Cys Val Pro Asn Ser Asn Glu Arg
        530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Glu Ala Trp Ala Lys Asp Leu Lys Leu Ala Asp Phe Ala
                580                 585                 590
```

```
Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
            645                 650                 655

Glu Thr Lys Asn Leu Leu Phe Asn Asp Asn Thr Glu Cys Leu Ala Arg
        660                 665                 670

Leu His Gly Lys Thr Thr Tyr Glu Lys Tyr Leu Gly Pro Gln Tyr Val
    675                 680                 685

Ala Gly Ile Thr Asn Leu Lys Lys Cys Ser Thr Ser Pro Leu Leu Glu
690                 695                 700

Ala Cys Glu Phe
705

(2) INFORMATION FOR SEQ ID NO:5:

(i) SEQUENCE CHARACTERISTICS:
        (A) LENGTH: 2086 base pairs
        (B) TYPE: nucleic acid
        (C) STRANDEDNESS: double
        (D) TOPOLOGY: linear (xi) SEQUENCE DESCRIPTION: SEQ ID NO:5:

CGAGGATCAT GGCTCACTGC CACCTTCATC TCCCAGGCTC AAATGGTCCT CCCACTTTAG      60

CCTCCCAAGT AGCTGGGACC ATAGGCATAC ACCACCATGC TGGGCTAATT TTTGTATTTT    120

TTGTAGAGAT GGGGGTTTCC CTATGAAGCC CAGGCTAGTC TTGAACTCCT GGGCTCAAGC    180

GATCCTCCCA TCTTGGCCTC CCAAAGTGCT GGGATTACAG GCATGAGCCA CTGTGCCCTG    240

CCTAGTTACT CTTGGGCTAA GTTCACATCC ATACACACAG GATATTCTTT CTGAGGCCCC    300

CAATGTGTCC CACAGGCACC ATGCTGTATG TGACACTCCC CTAGAGATGG ATGTTTAGTT    360

TGCTTCCAAC TGATTAATGG CATGCAGTGG TGCCTGGAAA CATTTGTACC TGGGGTGCTG    420

TGTGTCATGG GAATGTATTT ACGAGATGTA TTCTTAGAAG CAGTATTCTA GCTTTTGAAT    480

TTTAAAATCT GACATTTATG GCGATTGTTA AAATGAGGTT ACCATTTCCT ACTGAATACT    540

ATCAACACCA AAAAGAAGA AGGAGGAGAT GGAGAAAAAA AAGACAAAAA AAAAAAAAGT    600

GGTAGGGCAT CTTAGCCATA GGGCATCTTT CTCATTGGCA AATAAGAACA TGGAACCAGC    660

CTTGGGTGGT GGCCATTCCC CTCTGAGGTC CCTGTCTGTT TTCTGGGAGC TGTATTGTGG    720

GTCTCAGCAG GGCAGGAGA TACCCCATGG GCAGCTTGCC TGAGACTCTG GCAGCCTCT    780

CTTTTCTCTG TCAGCTGTCC CTAGGCTGCT GCTGGGGGTG GTCGGGTCAT CTTTTCAACT    840

CTCAGCTCAC TGCTGAGCCA AGGTGAAAGC AAACCCACCT GCCCTAACTG GCTCCTAGGC    900

ACCTTCAAGG TCATCTGCTG AAGAAGATAG CAGTCTCACA GGTCAAGGCG ATCTTCAAGT    960

AAAGACCCTC TGCTCTGTGT CCTGCCCTCT AGAAGGCACT GAGACCAGAG CTGGGACAGG   1020

GCTCAGGGGG CTGCGACTCC TAGGGGCTTG CAGACCTAGT GGGAGAGAAA GAACATCGCA   1080

GCAGCCAGGC AGAACCAGGA CAGGTGAGGT GCAGGCTGGC TTTCCTCTCG CAGCGCGGTG   1140

TGGAGTCCTG TCCTGCCTCA GGGCTTTTCG GAGCCTGGAT CCTCAAGGAA CAAGTAGACC   1200

TGGCCGCGGG GAGTGGGGAG GGAAGGGGTG TCTATTGGGC AACAGGGCGG GGCAAAGCCC   1260

TGAATAAAGG GGCGCAGGGC AGGCGCAAGT GGCAGAGCCT TCGTTTGCCA AGTCGCCTCC   1320

AGACCGCAGA CATGAAACTT GTCTTCCTCG TCCTGCTGTT CCTCGGGGCC CTCGGTGAGT   1380
```

```
GCAGGTGCCT GGGGGCGCGA GCCGCCTGAT GGGCGTCTCC TGCGCCCTGT CTGCTAGGCG    1440

CTTTGGTCCC TGTGTCCGGT TGGCTGGGCG CGGGGTCTCT GCGCCCCGCG GTCCCAGCGC    1500

CTACAGCCGG GAGGCGGCCC GGACGCGGGG CCAGTCTCTT TCCCACATGG GGAGGAACAG    1560

GAGCTGGGCT CCTCAAGCCG GATCGGGGCA CGCCTAGCTC TGCTCAGAGC TTCTCAAAAG    1620

GCCTCCCAGG CCCCTGTCCC TTTGTGTCCC GCCTAAGGAT TTGGTCCCCA TTGTATTGTG    1680

ACATGCGTTT TACCTGGGAG GAAAGTGAGG CTCAGAGAGG GTGAGCGACT AGCTCAAGGA    1740

CCCTAGTCCA GATCCTAGCT CCTGCGAGGA CTGTGAGACC CCAGCAAGAC CGAGCCTTTA    1800

TGAGACTTAG TTTCTTCACT TAAAGAAACG GCCTAACCAT GGGTCCACAG GGTTGTGAGG    1860

AGGAGATGGG GCATTCGCAC ACCTTCCGTG GCAGAGGGTT GTGGAGGGGT GCGGTGCTCC    1920

TGATGGAACC CTGTGTCAGA GGGTTTGAGA GGGAAATGTC AGCCAAACAG AAGGAAGGAG    1980

CAGAAGGAAG GAAACAATTG TCAGTTCCAT AACCAAAGTA ATTTCTCGGG TGCTCAGAGG    2040

GCACTCCCCA GCGCTGCACA TTAGTGACCT AAATGCGTGA GTGCGG                  2086
```